US010238301B2

(12) United States Patent
Weebadde et al.

(10) Patent No.: US 10,238,301 B2
(45) Date of Patent: Mar. 26, 2019

(54) VITAL MONITORING DEVICE, SYSTEM, AND METHOD

(71) Applicant: Avidhrt, Inc., East Lansing, MI (US)

(72) Inventors: Chandana Prabode Weebadde, Okemos, MI (US); Victor Karthik, Okemos, MI (US); Robert Alan Frank, Detroit, MI (US); Brian Collins, Seattle, WA (US)

(73) Assignee: Avidhrt, Inc., East Lansing, MI (US)

( * ) Notice: Subject to any disclaimer, the term of this patent is extended or adjusted under 35 U.S.C. 154(b) by 0 days.

(21) Appl. No.: 15/814,084

(22) Filed: Nov. 15, 2017

(65) Prior Publication Data

US 2018/0132735 A1    May 17, 2018

Related U.S. Application Data

(60) Provisional application No. 62/422,225, filed on Nov. 15, 2016.

(51) Int. Cl.
*A61B 5/0205*    (2006.01)
*A61B 5/00*    (2006.01)
(Continued)

(52) U.S. Cl.
CPC ........ *A61B 5/02055* (2013.01); *A61B 5/0006* (2013.01); *A61B 5/0008* (2013.01); *A61B 5/044* (2013.01); *A61B 5/0452* (2013.01); *A61B 5/14551* (2013.01); *A61B 5/6826* (2013.01); *A61B 5/7405* (2013.01);
(Continued)

(58) Field of Classification Search
None
See application file for complete search history.

(56) References Cited

U.S. PATENT DOCUMENTS

| 5,640,996 A | 6/1997 | Heden et al. |
| 5,919,141 A | 7/1999 | Money et al. |
(Continued)

FOREIGN PATENT DOCUMENTS

WO    2016123047    8/2016

OTHER PUBLICATIONS

International Search Report, dated Jan. 23, 2018 for PCT/US2017/061845.

*Primary Examiner* — Carl H Layno
*Assistant Examiner* — Qingjun Kong
(74) *Attorney, Agent, or Firm* — Loomis, Ewert, Parsley, Davis & Gotting PC; Mikhail Murshak

(57) ABSTRACT

The present disclosure generally relates to a portable vital monitoring system and a method for monitoring an individual's vitals using a portable vital monitoring system. The portable vital monitoring system includes a stand-alone portable vital monitoring device that allows the individual to detect or measure the individual's vitals. The stand-alone device includes a plurality of sensing devices for detecting data indicative of the individual's vitals and generating one or more signals indicative of the vital data. The system also includes a control unit connected to the sensing devices for processing the signal such that the data can be displayed to and understood by the individual. The system also includes a vital monitoring application in wireless communication with the vital monitoring device via a wireless communication module.

18 Claims, 31 Drawing Sheets

(51) Int. Cl.
*A61B 5/0452* (2006.01)
*A61B 5/044* (2006.01)
*A61B 5/1455* (2006.01)
*A61B 5/024* (2006.01)

(52) U.S. Cl.
CPC .......... *A61B 5/7435* (2013.01); *A61B 5/7455* (2013.01); *A61B 5/02444* (2013.01)

(56) References Cited

U.S. PATENT DOCUMENTS

| | | | |
|---|---|---|---|
| 6,571,114 B1* | 5/2003 | Koike | A61B 5/02416 600/323 |
| 7,020,508 B2 | 3/2006 | Stivoric et al. | |
| 8,255,238 B2 | 8/2012 | Powell et al. | |
| 8,923,918 B2 | 12/2014 | Kreget et al. | |
| 9,028,404 B2 | 5/2015 | DeRemer et al. | |
| 9,183,351 B2 | 11/2015 | Shusterman | |
| 2004/0068195 A1 | 4/2004 | Massicotte et al. | |
| 2007/0180047 A1 | 8/2007 | Dong et al. | |
| 2007/0276262 A1 | 11/2007 | Banet et al. | |
| 2010/0095439 A1* | 4/2010 | Nolan | A42B 3/24 2/421 |
| 2011/0224499 A1 | 9/2011 | Banet et al. | |
| 2012/0156933 A1* | 6/2012 | Kreger | A61B 5/02433 439/625 |
| 2013/0310659 A1* | 11/2013 | Kawachi | A61B 5/0404 600/301 |
| 2014/0100432 A1 | 4/2014 | Golda et al. | |
| 2014/0206955 A1 | 7/2014 | Stivoric et al. | |
| 2014/0243621 A1 | 8/2014 | Weng et al. | |
| 2014/0278552 A1 | 9/2014 | Hold | |
| 2015/0172893 A1 | 6/2015 | St. Germain et al. | |
| 2015/0335283 A1* | 11/2015 | Fish | A61B 5/02416 600/324 |
| 2016/0066808 A1 | 3/2016 | Hijazi | |
| 2016/0120430 A1* | 5/2016 | Bayasi | A61B 5/0456 600/516 |
| 2016/0225192 A1 | 8/2016 | Jones et al. | |
| 2016/0228025 A1 | 8/2016 | Dusan | |
| 2017/0055869 A1* | 3/2017 | Shin | A61B 5/04288 |

* cited by examiner

VITAL MONITORING DEVICE, SYSTEM, AND METHOD

CROSS REFERENCE TO RELATED APPLICATION

Priority is claimed to U.S. Provisional Application No. 62/422,225 filed Nov. 15, 2016, which is incorporated herein by reference in its entirety.

FIELD OF DISCLOSURE

The present disclosure generally relates to a portable vital monitoring system and method and in particular, to a stand-alone vital monitoring device and an associated vital monitoring application accessible on a smart device. A method for monitoring an individual's vitals using the stand-alone vital monitoring device and associated vital monitoring application is also provided.

BACKGROUND OF THE DISCLOSURE

Health monitoring and vital measuring machines in hospital settings are well-known. These machines are used to measure or monitor a patient's vitals such as, body temperature, respiratory rate, blood pressure, electrocardiography (electrocardiogram), pulse oximetry, and the like. However, these machines are typically separate from one another such that only a single vital is measured at a time and may require up to twelve (12) electrode leads or a number of different sensors to measure a single vital. For instance, the machine for conducting an electrocardiogram (ECG) requires between three (3) and ten (10) electrodes with exact placement on three (3) and ten (10) points of the patient's body to detect electrical activity of the heart. If exact placement of the electrodes is not achieved, then the measurements will be incorrect which can result in an improper or false diagnosis. A second machine would be required to monitor a different vital, such as respiratory rate or pulse oximetry, which would have its own set of electrodes or sensors as well.

The electrodes or sensors for detecting a particular vital, are connected to the machine through a set of wires, and transmit data relating to the patient's vitals to the machine for processing and analysis by the doctor. Additionally, current machines are often stationary, bulky, and can be heavy to transport between patient rooms. Accordingly, the patient may be covered in multiple wires and will be restricted to only moving as far as the length of the wiring since the machine cannot be moved.

The machines may also have a display integrated therein or may be attached a separate piece of equipment, equally as bulky, through a wired connection. The display shows a graphical or numerical representation of the data obtained by the electrodes. A doctor may review the graphical and/or numerical data on the display or may print the data to analyze and determine if any treatment is necessary. In the past, the print out of the data was added to the patient's medical file. In recent years, those files have been converted into an electronic medical records system, which allows the patient's records to be electronically available on the hospital's individual network. Accordingly, the patient's vital data may be manually or automatically added to the patient's electronic medical records by the doctor or nurse while measurements are taken, which will then become accessible by any computer on the hospital individual network. Alternatively, the machines may be directly connected to the hospital's individual network via a wired or wireless connection and may transmit the data to the patient's medical record. However, these records may not be accessible outside of that particular hospital/hospital network and may not be accessed by or sent to a third party easily for a medical consult.

These systems and machines are very costly to purchase and maintain. As such, each machine's presence is limited and may even require the patient to travel to different rooms to have each vital monitored.

Further, due to the cost and size of these machines, some medical clinics cannot afford to purchase and maintain these machines. Accordingly, these medical clinics are unable to monitor such vitals and would be required to send patients elsewhere to run test or obtain diagnosis and treatment. As such, valuable time is wasted, not to mention, the costs of running the tests are equally as expensive due to the size and costs associated with operating and maintaining the machines. Similarly, traveling medical professions who treat army personnel, athletes, or individuals in areas of countries that do not have access to large medical clinics, hospital, or the machines, cannot monitor such vitals.

Thus, there is a need for a vital monitoring system which is small or compact, lightweight, portable, inexpensive and cost effective such that patients, medical professionals in the field, and small, medium, and large clinics or hospitals can easily obtain and access them. Further, a vital monitoring system is needed that provides a way for third parties to easily access the patient's data in the event a medical consult is required.

SUMMARY OF THE DISCLOSURE

The present disclosure provides for a vital monitoring device. The device includes a control unit enclosed in a housing. The control unit includes a microprocessor provided on a circuit board having a plurality of channels for receiving and processing sensor data. Each of the plurality of channels is coupled to the microprocessor. The device further includes a plurality of sensors coupled to the control unit and operable for obtaining at least three vitals from a user including pulse oximetry, electrocardiogram (ECG), and skin temperature. Each of the plurality of sensors is coupled to at least one of the plurality of channels and operable for generating signals indicative of the obtained vitals. The control unit further includes a wireless communication module coupled to the microprocessor. The wireless communication module is adapted to transmit vital data obtained by the plurality of sensors to a remote application or remote server. In one example, the plurality of sensors include a pulse oximetry sensor, an ECG sensor, and a temperature sensor, and each of the pulse oximetry sensor, ECG sensor, and temperature sensor are electronically coupled to a separate and distinct channel formed on the circuit board.

The present disclosure further provides for a system for vital monitoring of a user. The system includes a vital monitoring device having: (i) a control unit enclosed in a housing, the control unit including a microprocessor provided on a circuit board having a plurality of channels for receiving and processing sensor data, each of the plurality of channels coupled to the microprocessor; (ii) a plurality of sensors coupled to the control unit and operable for obtaining at least three vitals from a user including pulse oximetry, electrocardiogram (ECG), and skin temperature, wherein each of the plurality of sensors is coupled to at least one of the plurality of channels and operable for generating signals indicative of the obtained vitals; and (iii) a wireless communication module coupled to the microprocessor, wherein the wireless communication module is adapted to transmit vital data obtained by the plurality of sensors. The system further includes a remote application hosted on a remote device operable for wirelessly communicating with the vital monitoring device and receiving the vital data transmitted by the wireless communication module. A graphical user interface is provided on the remote application and adapted to display vital data obtained by the vital monitoring device. In one example, the plurality of sensors are each accessible on the exterior surface of the housing at separate sensor locations including a first finger depression sized and shaped to receive a first finger of the user, a second finger depression sized and shaped to receive a second finger of the user, and a third finger placement location sized and shaped to receive a third finger of the user.

The present disclosure further provides for a method of monitoring vital data of an individual. The method includes the steps of: (a) placing a vital monitoring device, as described above, in contact with a body of an individual; (b) obtaining pulse oximetry, ECG, and temperature vital data of the user using the vital monitoring device; (c) transmitting the vital data to a mobile application through the wireless communication module; (d) graphically displaying the vital information to the user through the remote application; and (e) optionally transmitting vital monitoring data to a remote server.

The aspects of the present disclosure present various advantages over current systems. For instance, the vital monitoring system offers a portable, small, compact, accessible, and cost effective solution to issues associated with current vital measuring machines. The system also provides the ability to use a single device to measure or detect multiple types of an individual's vitals. Further, the system provides the ability to access and analyze the vital data easily and in real-time through a vital monitoring application, wirelessly transmit the vital data to a server, generate intervention alerts generated by machine learning algorithm using vital, physical, diet and habits/addiction data of the individual and access analyses from a remote location by authorized users and by the individual.

BRIEF DESCRIPTION OF THE DRAWINGS

Other aspects of the present disclosure will become better understood by reference to the following description when considered in connection with the accompanying drawings wherein:

FIG. 8A shows a connection screen, FIG. 8B shows measurements for a main display interface, FIG. 8C shows graphical representations of heart activity, FIG. 8D shows a patient identification interface, FIG. 8E a patient specific monitoring interface.

FIG. 10A is a perspective front view of the dedicated device, FIG. 10B is a side and front face view of the dedicated device, FIG. 10C is a perspective view in use with fingers of a user of the dedicated device, and FIG. 10D illustrates a disassembled view of the dedicated device;

DETAILED DESCRIPTION OF THE PRESENT DISCLOSURE

Figure 1:
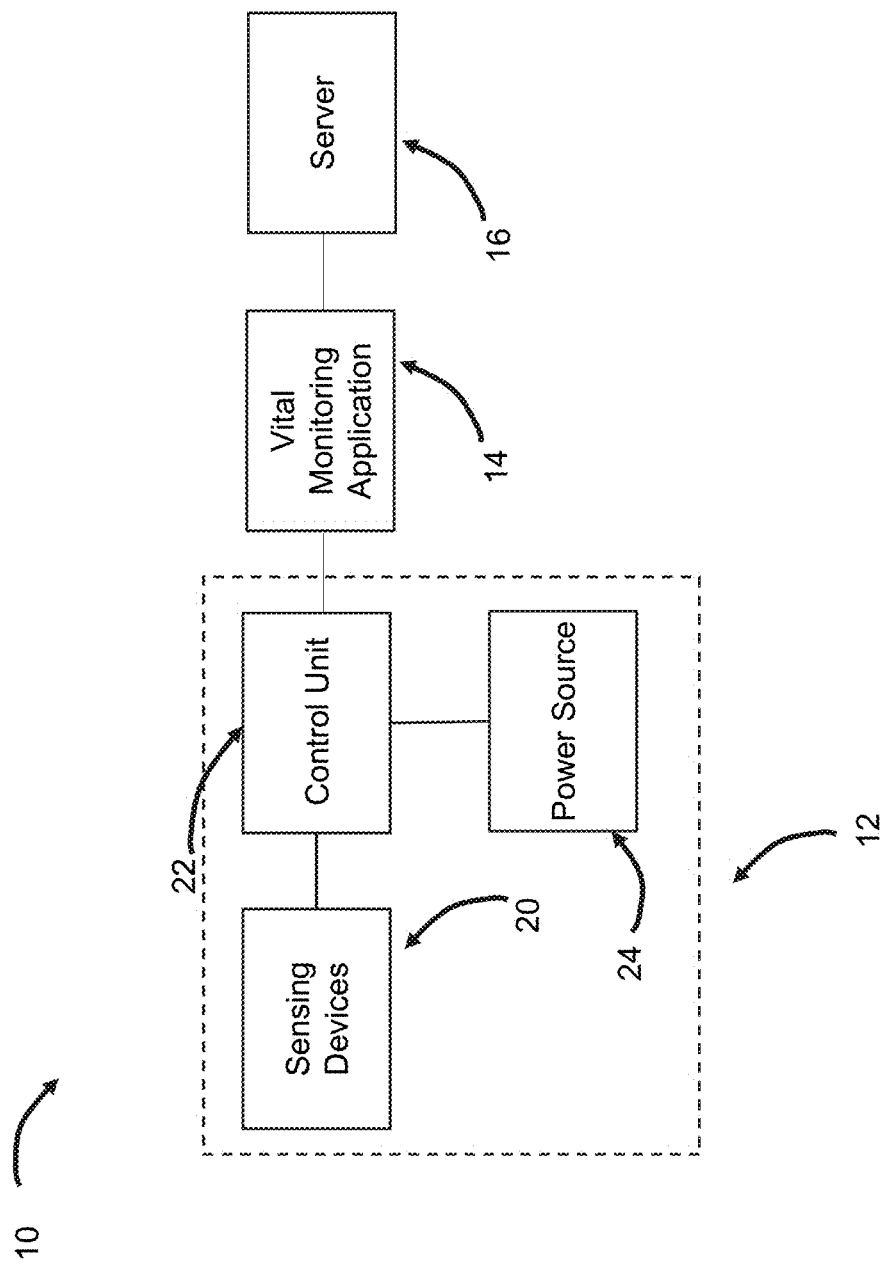
FIG. 1 is a block diagram of a portable vital monitoring system in accordance with an aspect of the present disclosure.

Detailed aspects of the present disclosure are provided herein; however, it is to be understood that the disclosed aspects are merely exemplary and may be embodied in various and alternative forms. It is not intended that these aspects illustrate and describe all possible forms of the disclosure. Rather, the words used in the specification are words of description rather than limitation, and it is understood that various changes may be made without departing from the spirit and scope of the disclosure. As those of ordinary skill in the art will understand, various features of the present disclosure as illustrated and described with reference to any of the Figures may be combined with features illustrated in one or more other Figures to produce examples of the present disclosure that are not explicitly illustrated or described. The combinations of features illustrated provide representative examples for typical applications. However, various combinations and modifications of the features consistent with the teachings of the present disclosure may be desired for any particular applications or implementations. Additionally, the features and various implementing embodiments may be combined to form further examples of the disclosure.

The aspects of the present disclosure provide for a portable vital monitoring system and a method for monitoring an individual's vitals using a portable vital monitoring system. The portable vital monitoring system includes a stand-alone portable vital monitoring device that allows a doctor or the individual themselves to detect or measure the individual's vitals. In doing so, the stand-alone device includes two or more sensing devices, such as electrodes, a sensor, or another sensing device, for detecting data indicative of the individual's vitals and generating one or more signals indicative of the vital data. The portable vital monitoring system also includes a control unit connected to the sensing devices for processing the signal such that the data can be displayed to and understood by the doctor or individual. The individual's vitals measurements/data include electrocardiogram (ECG), pulse oximetry, and skin temperature. The stand-alone device is compact, lightweight, low-power, and cost effective, as the device costs around $5 or less to manufacture.

The portable vital monitoring system also includes a vital monitoring application that is accessible and compatible with any smart device, such as a smart phone, a tablet, a smart watch, a computer, laptop, or the like. The stand-alone device is in wireless communication with the vital monitoring application via a wireless communication protocol, such as BLUETOOTH®, BLUETOOTH® Low Energy, ZIGBEE®, WLAN, 3G/4G, or the like, of a smart device and transmits the signal indicative of vital data to the vital monitoring application for display and analysis in real-time. The vital monitoring application has multiple graphical user interfaces for graphically and numerically displaying the data obtained from the sensing devices. The vital monitoring application employs a machine learning algorithm that is configured to provide early intervention alerts for long-term users by analyzing data transmitted from two or more data channels, two or more channels may include ECG, pulse oximetry, activity, position, respiratory rate, galvanic skin response, perspiration, sleep patterns, global positioning, metabolic parameters, stress, skin temperature, physical activity, diet or habits/addiction. The machine learning algorithm analyzes and compares the data from the combination of two or more channels, one or more vital sensors, and/or one or physical activity, diet and habits/addition recordings to determine if any abnormality exist. For example, from the ECG obtained, the algorithm would alert heart rate, rhythm, if it is symptomatic of Atrial fibrillation (Afib), or Premature ventricular contractions (PVCs). In another example, the heart rate obtained from an ECG and pulse oximetry would be compared and if it were abnormal, data from blood pressure, activity, habits and temperature would then be considered for further analysis. The portable vital monitoring system may also include a server in communication with the vital monitoring application. The server is designed to store the data relating to the individual's vitals, and is equipped with control logic for analyzing the data to determine changes, patterns or anomalies in the individual's vitals, in real-time or in the future from past stored data. The vital monitoring application can alert the individual or the doctor in the event an anomaly is detected. The server may also transmit the individual's vital data to a remote location, such as a hospital or medical clinic, for review by a doctor or another medical professional.

As it will become readily apparent to one skilled in the art, the portable vital monitoring system and method offers a lightweight, small, compact, and cost effective solution to current vital measuring machines.

FIG. 1 is a block diagram of a portable vital monitoring system 10 in accordance with an aspect of the present disclosure. As discussed above, the portable vital monitoring system 10 is designed to easily measure and/or detect two or more of an individual's vitals, such as electrocardiogram (ECG) (i.e., electrical activity in the individual's heart), pulse oximetry (i.e., levels of oxygen in the individual's blood), skin temperature, and the like, using a single device. The portable vital monitoring system 10 is also designed to easily display and analyze the individual's vitals such that appropriate treatment may be provided to the individual. The portable vital monitoring system 10 may be used by one or more medical professional, such as doctors or nurses, a third-party caregiver, the individual, or a combination thereof.

The portable vital monitoring system 10 includes a stand-alone portable vital monitoring device 12 and a vital monitoring application 14 in communication with the stand-alone portable vital monitoring device 12. The stand-alone device 12 detects and processes data indicative of the individual's vitals, while the vital monitoring application 14 organizes and displays the data indicative of the individual's vitals on a smart device for review and analysis by the medical professional, a third-party caregiver, the individual, or a combination thereof. The portable vital monitoring system 10 may further include a server 16 also in communication with the vital monitoring application 14. Additionally, the server 16 stores the data indicative of the individual's vitals and may further analyze the data to determine, changes, patterns or anomalies in the individual's health.

The stand-alone portable vital monitoring device 12 includes two or more sensing devices 20 configured to be disposed on or around the individual's body or skin. In one aspect of the present disclosure, device 12 includes at least 3 sensing devices 20 operable for measuring skin temperature, heart-related vital data, and pulse oximetry. For purposes of this application, the term "individual" is synonymous and interchangeable with the terms "user" and/or "patient". The sensing devices 20 detect events that occur within the individual's body and generates an output signal indicative of the detected events (i.e., vital data and information).

Figure 3A:
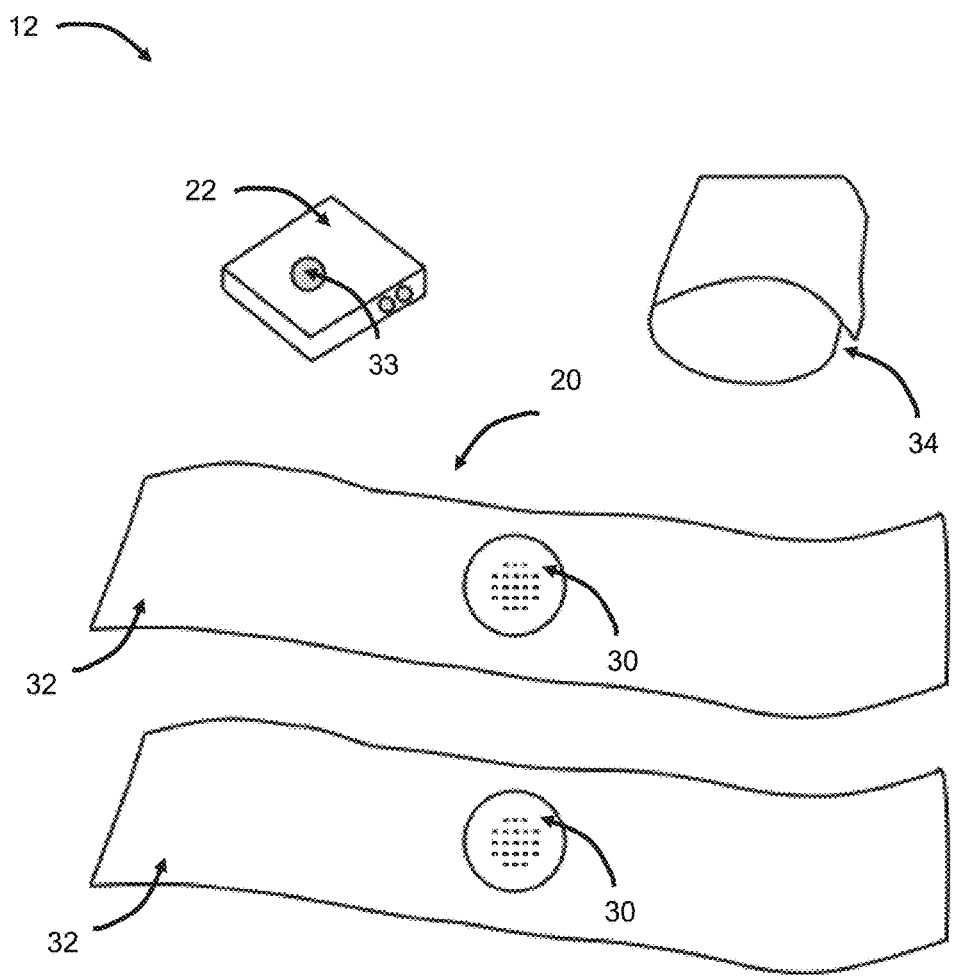
FIG. 3A illustrates a portable vital monitoring device of a portable vital monitoring system in an unwired state in accordance with an aspect of the present disclosure.
Figure 3B:
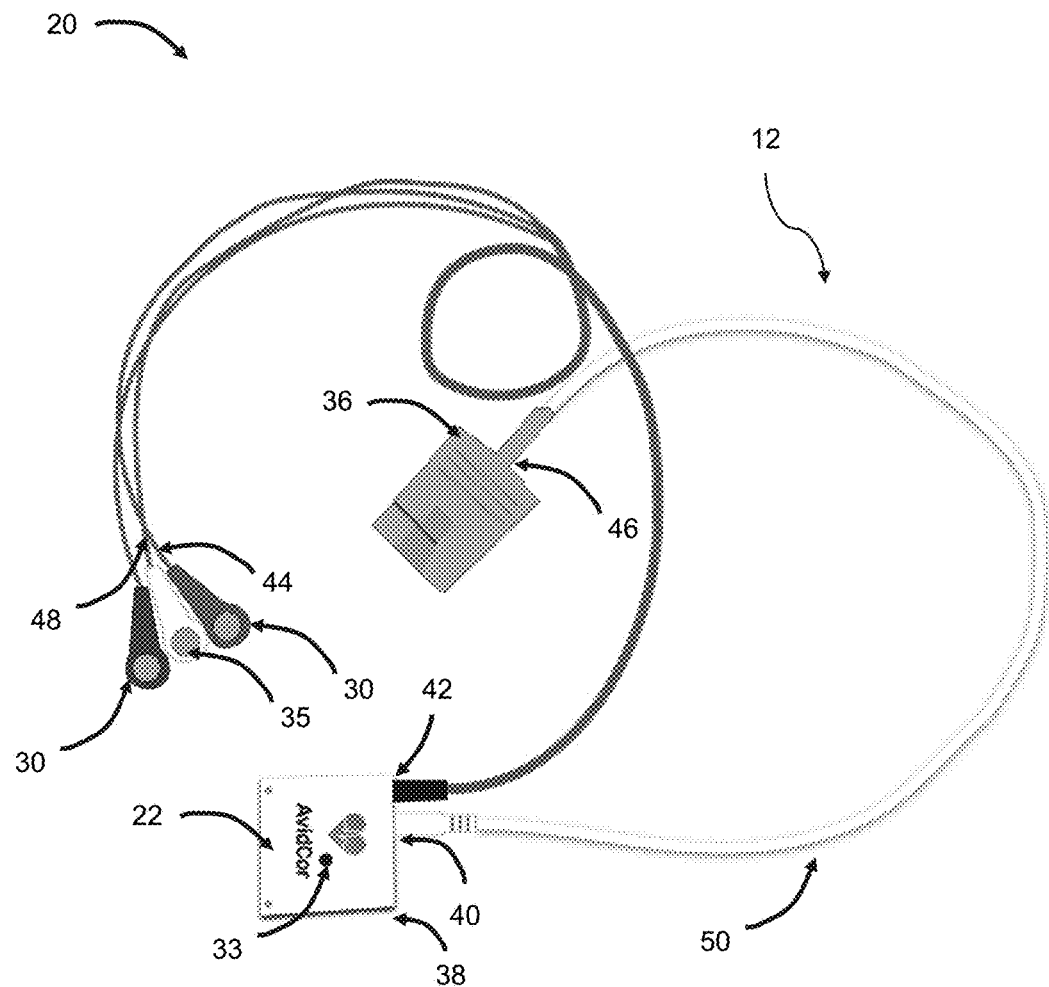
FIG. 3B illustrates a portable vital monitoring device of a portable vital monitoring system in a wired state in accordance with an aspect of the present disclosure.

The sensing devices 20 may include two electrodes 30 for detecting electrical changes (e.g., voltage, current changes) in the individual's heartbeat pattern. To detect these changes the electrodes 30 are placed in physical contact with an individual, ideally the individual's skin. The electrodes 30 can be incorporated into wearable devices, as shown in FIGS. 3A and 3B, which are each placed on the individual. For example, the wearable devices may be adjustable wristbands 32 that are placed around the individual's wrist. One skilled in the art appreciates that the wristbands are an example of a type of wearable device and is not meant to be limiting as other wearable devices may be employed.

Figure 7A:
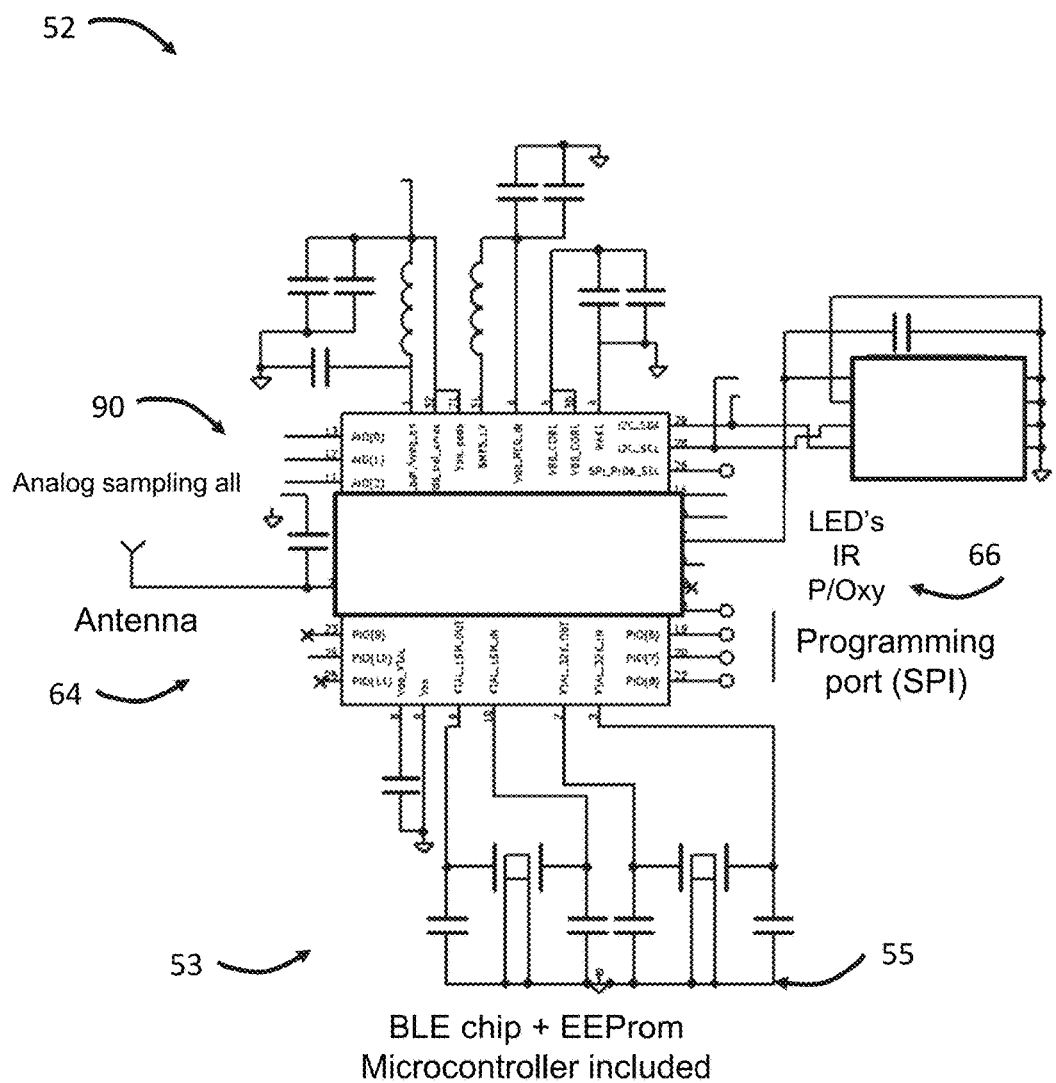
FIG. 7A shows a circuit diagram for a microcontroller included control unit of a portable vital monitoring device in accordance with an aspect of the present disclosure.
Figure 7B:
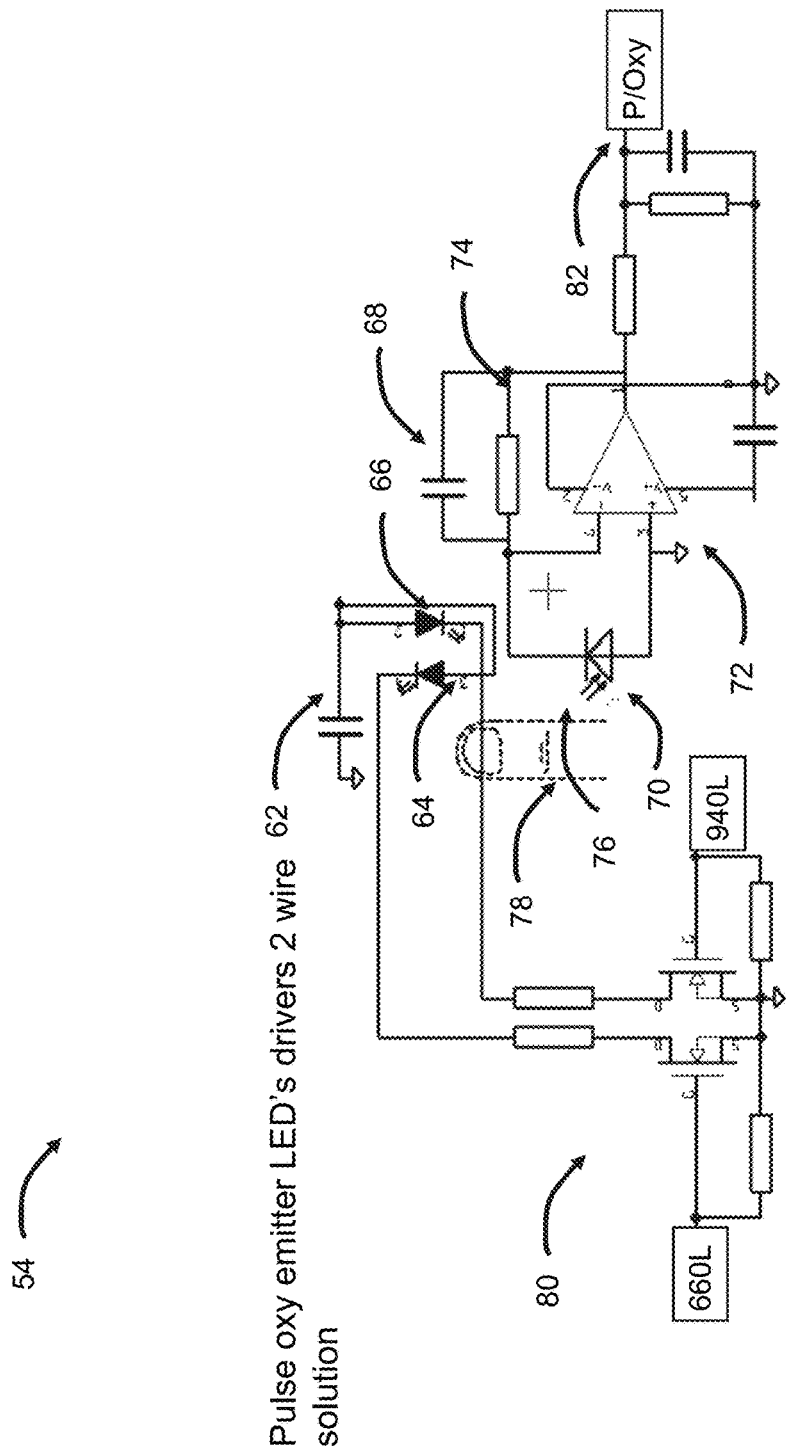
FIG. 7B shows a circuit diagram for a pulse oxy emitter provided for a control unit of a portable vital monitoring device in accordance with an aspect of the present disclosure.

The sensing devices 20 may include a pulse oximetry sensor having a pair of light-emitting diodes and a photo-detector (i.e., photodiode) for detecting the absorption of light against the individual's skin to determine the individual's blood oxygen levels. The pulse oximetry sensor is operable for measuring the oxygen saturation within the individual's blood and can generate a signal indicative of the same. The circuit configuration of the pulse oximetry sensor is shown in FIG. 7B. Like the electrodes 30, the pulse oximetry sensor 36 can be incorporated into a wearable device, such as those shown in FIG. 3A. For instance, the sensor may be incorporated into an adjustable finger band 34 or a pulse oximeter box 36 that receives the individual's finger. One skilled in the art appreciates that the finger band 34 or pulse oximeter box 36 are examples of types of wearable devices and is not meant to be limiting as other wearable devices may be employed.

Figure 5:
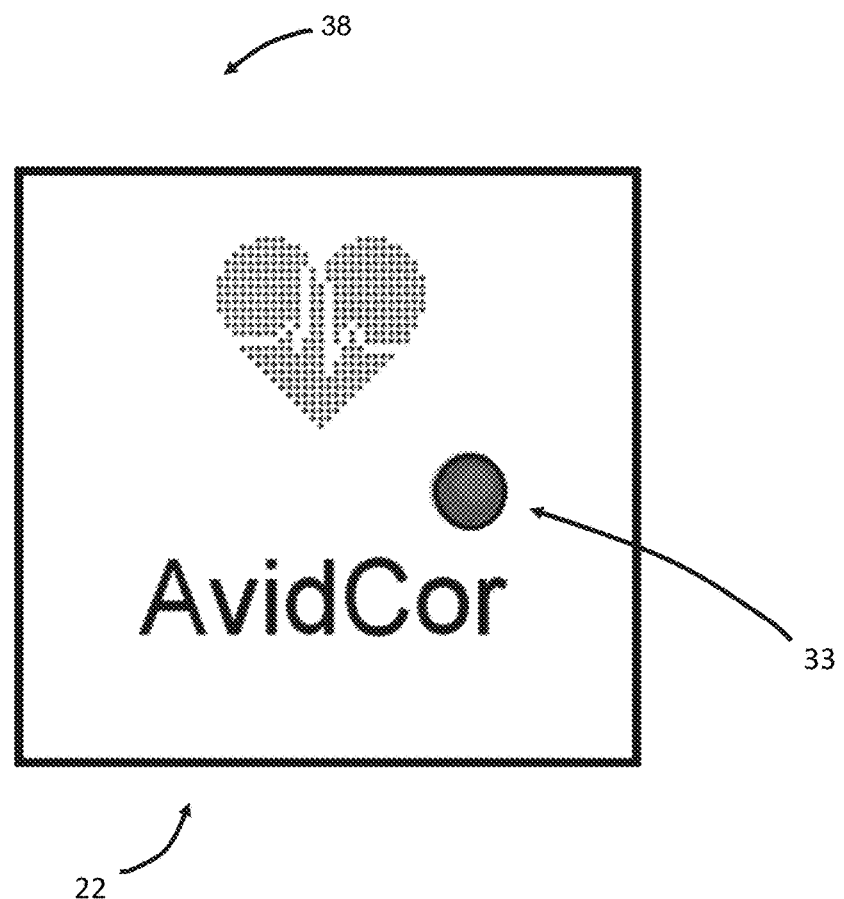
FIG. 5 is an illustration of a control unit with a temperature sensor in accordance with an aspect of the present disclosure.

The sensing devices 20 can further include a temperature sensor 33 consisting of a thermistor for measuring skin temperature of the individual. The temperature sensor 33 is operable to generate a signal indicative of the same. In an aspect of the present disclosure, the temperature sensor 33 may be integrated into a control unit 22, which is described in further detail below and is shown in FIG. 5. A circuit schematic for control unit 22 is shown in FIG. 7A. In an alternative aspect, the temperature sensor 33 may be integrated into either a wristband 32 with the electrodes 30 or a finger band with the pulse oximetry sensor 36.

In one example of the present disclosure, a control unit 22 is electrically connected to two or more sensing devices 20. In another aspect of the present disclosure, the control unit 22 is electrically connected to two or more sensing devices through a wired connection, as shown in FIGS. 3A and 3B. Outputs of the sensing devices 20 are connected to inputs of the control unit 22. In yet another aspect, the sensing devices 20 may have wireless communication modules, such as BLUETOOTH®, WLAN, or another wireless communication technology known in the communication field, and thus may be able to wireless connect to the control unit 22 to transmit signals. In yet a further embodiment, control unit 22 is coupled to at least three sensing devices 20.

The control unit 22 is operable to receive and process signals obtained from the sensing devices 20. Specifically, the control unit 22 includes one or more individualized circuits and a microprocessor for analyzing, filtering, and converting the signals from the sensing devices 20. This includes converting signals from analog and digital signals. In one example, a power supply 24 is connected to and powers the control unit 22. The power supply 24 can be any battery including a 3V cell or other type. In one form, the portable vital monitoring device 12 can operate on low-power and under less than 1 mA. As such, there is little to no harm associated with electrical contact to the individual's body in using the device 12.

In yet another example, the microprocessor of the control unit 22 is also equipped with a wireless communication protocol, such as BLUETOOTH®, BLUETOOTH® Low Energy (BLE), or the like, and can transmit the converted digital signals to a BLUETOOTH® or wireless enabled device. The control unit 22 of the portable vital monitoring device 12 is operable to wirelessly communicate with a vital monitoring application 14 and transmit the converted digital signals to the vital monitoring application 14 for display on any device including smart device, so data can be reviewed by a medical professional, third party, and/or the individual. According to the present disclosure, the vital monitoring application 14 can be a mobile application and can be made accessible and compatible with any operating system of various web-enabled smart devices and may be downloaded onto the smart device. The smart devices may include, but are not limited to, a smart phone, a smart watch, a tablet, a computer, laptop, and the like.

The vital monitoring application 14 may employ a machine learning algorithm configured to provide early intervention alerts for long-term users by analyzing data coming from a combination of two or more channels, one or more vital sensors, and one or more physical activity, diet and habits/addiction recordings. The vital monitoring application 14 includes various graphical user interfaces to display graphical and/or numeric representation of the signals obtained from the sensing devices 20. For instance, each vital detected by the sensing devices 20 can have its own graphical user interface. For example, there may be an ECG graphical interface for displaying the electrical activity of the individual's heart, a pulse oximetry graphical interface for the individual's pulse oximetry levels, and a skin temperature graphical interface for displaying the individual's body temperature. The vital monitoring application 14 is described in greater detail below with reference to FIGS. 8A-8E.

In yet a further example, an ambient temperature sensor (not shown) is provided and included in the device 12 coupled to control unit 22. When temperature data is obtained, collected and processed, a comparison of the ambient and body temperature of the user can be compared to identify high risk environmental conditions. For example, if the user is involved in a high stress environment, such as a fire fighter, the temperature difference between body temperature and ambient temperature can be tracked and monitored to determine warning signals for high risk and dangerous conditions.

In one example, the vital monitoring application 14 is in communication with the server 16. The vital monitoring application 14 may upload and transmit the graphical and numerical representation of the individual's vital data to the server 16 through an internet, broadband, or data connection such as 3G, 4G, LTE or the like. The server 16 can be a cloud network server and can be provided to medical professionals, third-party caregivers, or individuals that utilize the vital monitoring application 14. The server 16 can also be a secured network and encrypted to maintain privacy of the individual's vital data uploaded and transmitted to the server 16.

In an example, the server 16 has a central processing unit (not shown) equipped with one or more processors (not shown) for reviewing and analyzing the individual's vital data uploaded to the server 16 and one or more memory storage mediums (not shown) for storing the individual's vital data for real-time and/or future analysis. The processors are programmed with control logic for performing analysis on the individual's vital data stored therein. To do so, the vital data is reviewed and may be compared against newly uploaded data to detect if any, change, event, or anomaly has occurred. If an event or an anomaly is detected, the server 16 generates an alert and transmits the alert to the vital mobile application 14.

Figure 2:
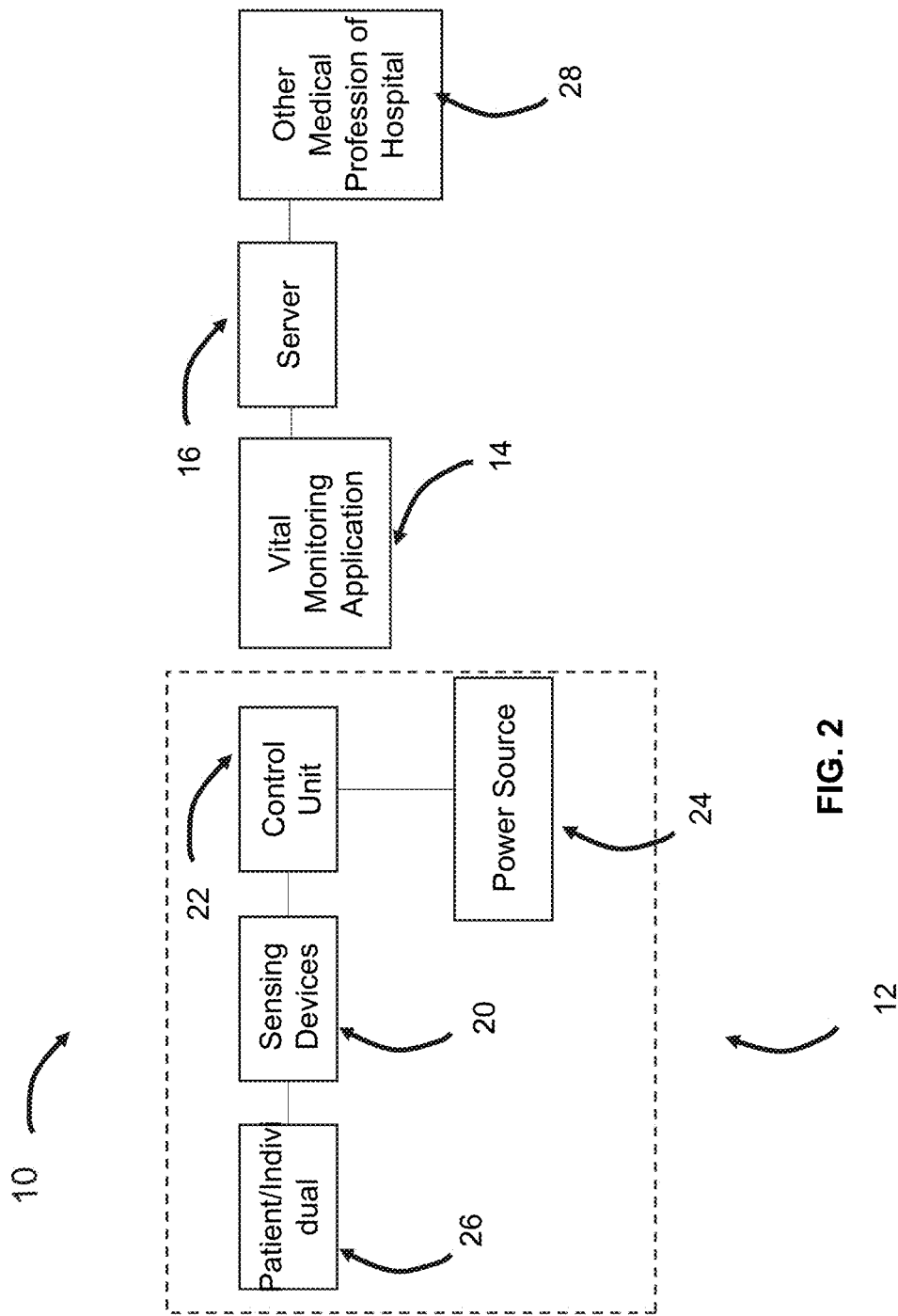
FIG. 2 is another block diagram of a portable vital monitoring system in accordance with an aspect of the present disclosure.

FIG. 2 is also a block diagram that includes additional aspects to FIG. 1. Particularly, FIG. 2 shows that the sensing devices 20 are in contact with an individual 26 as discussed above. Additionally, FIG. 2 shows the server 16 may also communicate with and transmit the individual's vital data to a third party 28, such as other medical professionals or a hospital, at a remote location from the individual 26. Communication may occur through an internet, broadband, or data connection discussed above. This enables the third party 28 to review the individual's vital data in a remote location for medical purposes, such as a second opinion or a medical consultation from a specialist with expertise in a particular location different from where the individual is located. For example, an individual 28 and a doctor in Sri Lanka can transmit the individual's 26 vitals measurements taken from the stand-alone device 12 through the server 16 to a doctor (third party 28) in the United States for a medical consultant. In another example, a doctor, who is on vacation, may receive updates on his/her patient/individual 26 whose vitals are being measured by the device 12 at the hospital. The vital data may be transmitted from the server 16 to a smart device equipped with the vital monitoring application 14 or alternatively, to a hospital's electronic medical records system. In one form, the third party 28 would have to be authorized by the individual 26 or his/her doctor to view the vital data. One skilled in the art appreciates the network is designed to be fully secure and in compliance with the same standards associated with security in electronic medical records.

FIGS. 3A-3B are illustrations of a portable vital monitoring device 12 of a portable vital monitoring system 10 in accordance with an aspect of the present disclosure as discussed in FIG. 1. FIG. 3A shows a portable vital monitoring device 12 in an unwired state. FIG. 3B shows a portable vital monitoring device 12 in a wired state. As discussed in FIG. 1, the portable vital monitoring device 12 has two or more sensing devices 20. The sensing devices 20 includes two (FIG. 3A) or three (FIG. 3B) electrodes 30, each of which are incorporated into a wearable device 32. In the example of the wristband, each wristband 32 with its own electrode 30 is placed around the individual's wrist to detect vital data and particularly, ECG measurements. The electrodes 30 are also shown in FIG. 3B. Specifically, the first electrode 30 may be used for the right arm, the second electrode 30 may be used for the left arm, and the third electrode 35 may be used as a reference to eliminate the common-mode voltage which may be placed proximate to the first or second electrode 30 or on another part of the individual's body.

Figure 6A:
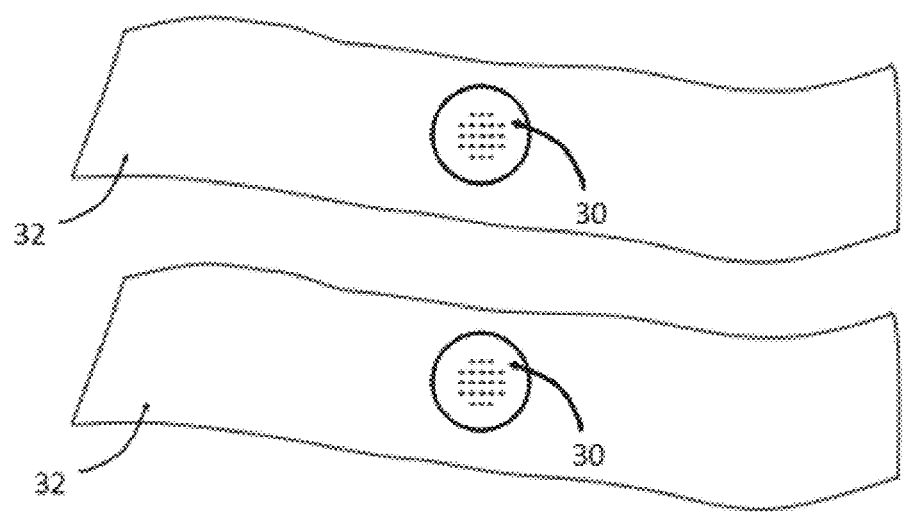
FIG. 6A illustrates example wristband electrodes of a portable vital monitoring device in accordance with an aspect of the present disclosure.
Figure 6B:
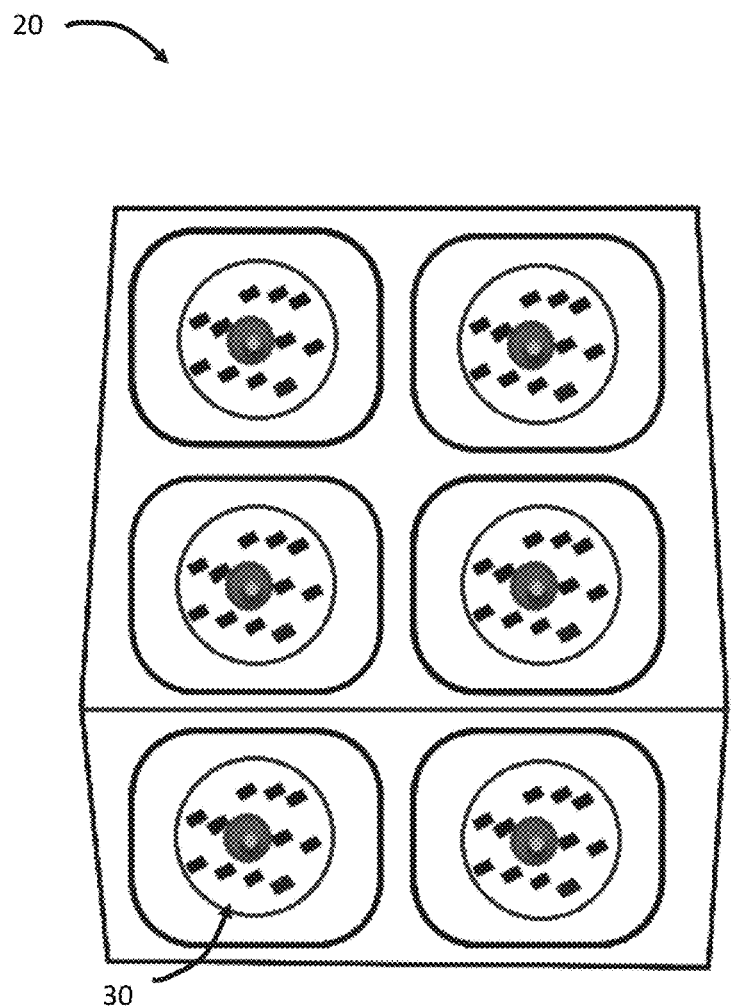
FIG. 6B illustrates example gel electrodes that are disposable and removable from the wristbands in accordance with an aspect of the present disclosure.

The sensing devices may 20 also include a sensor incorporated into a finger band 34 for measuring pulse oximetry levels of the individual. The finger band 34 is placed around the individual's finger such that the sensor is adjacent or is proximate to the individual. Alternatively, as shown in FIG. 3B, the finger band 34 may be replaced with a pulse oximetry box 36. The electrodes 30 and sensor (not shown) each have an output (also not shown) for receiving a wire or cable. Other alternatives may include a sensor for skin-based reflective measurement of pulse oximetry as well an electrode with a single lead and "phantom" or a virtual second lead for ECG measurements. The electrodes 30 as shown in both FIGS. 3A and 3B can be dry reusable electrodes, which are incorporated into the wristbands 32, as shown in FIG. 6A, or can be gel electrodes that are disposable and removable from the wristbands, as shown in FIG. 6B.

The portable vital monitoring device 12 further includes a control unit 22, as described above in FIG. 1, which will be described in more detail in FIGS. 4-7F. The control unit 22 includes a housing 38, which is relatively small and compact, and a set of inputs 40, 42 for receiving wires from the sensing devices 20 or will have the sensing devices incorporated within it. As shown in FIG. 3B, the electrodes 30 each have an output 44 and the pulse oximetry box 36 has an output 46 that is connected through cables 48 and 50, respectively. In operation, when the sensing devices 20 are in contact with, or proximate to, the individual and detect his/her vital data, one or more signals indicative of the vital data is generated and transmitted through the cables to the control unit 22 for processing. The body temperature sensor 33 could be incorporated into one of the wristbands 32 or finger band 34. Alternatively, the temperature sensor 33 may be incorporated into the control unit 22, as shown in FIG. 5 and accessed by placing on a user's body and touching it with the user's finger.

Figure 4:
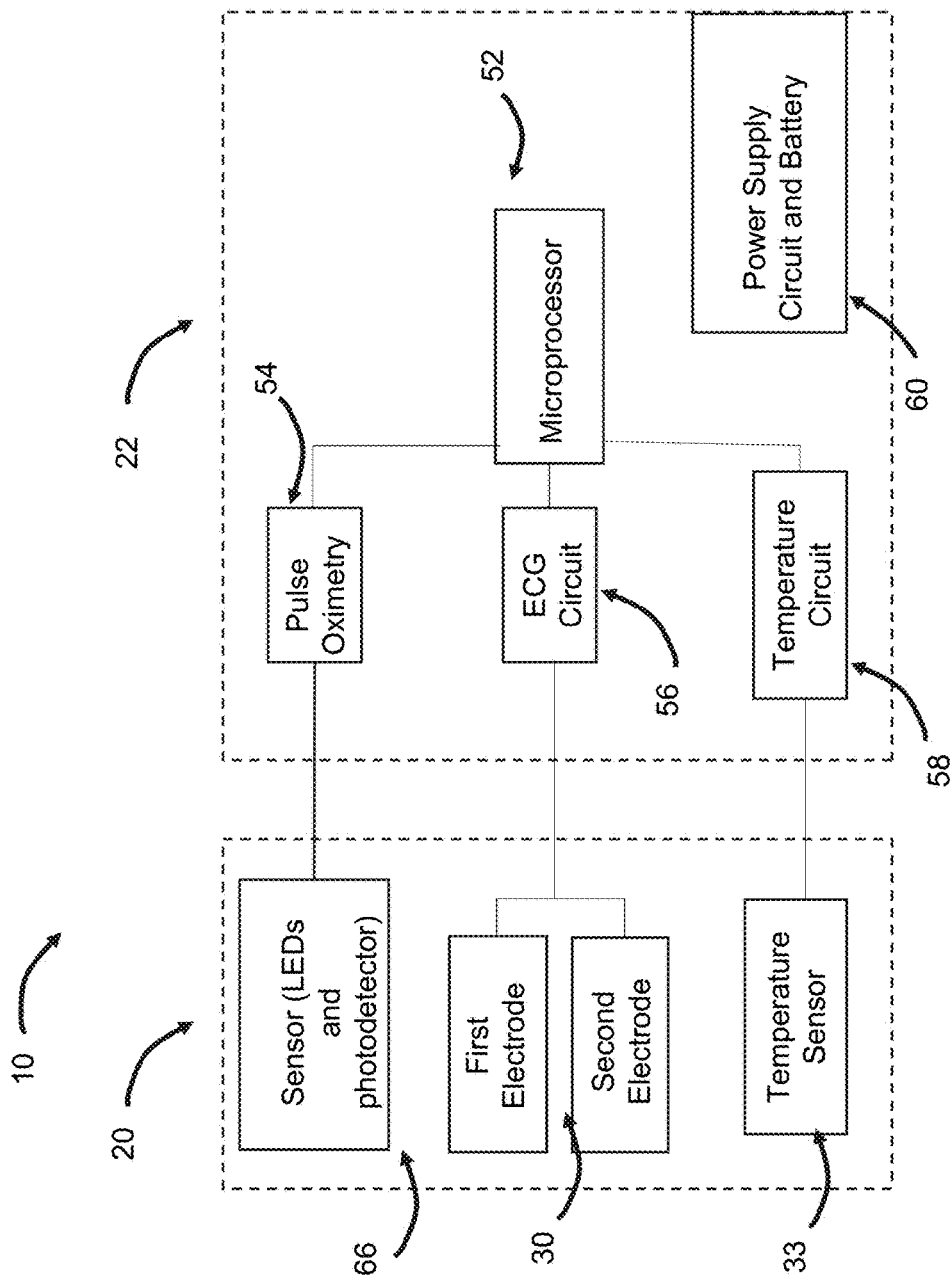
FIG. 4 is a block diagram of a control unit of a portable vital monitoring system in accordance with an aspect of the present disclosure.

FIG. 4 is a block diagram of a control unit 22 of a portable vital monitoring system 10 in accordance with an aspect of the present disclosure. The control unit 22 is designed to receive and read the signals indicated from vital data from each of three sensing devices, amplify the signals, filter the signals to remove unwanted frequencies and reduce background noise, and convert the signals from analog to digital. The control unit 22 includes a microprocessor 52, a pulse oximetry circuit 54, an ECG circuit 56, a temperature circuit 58, and a power supply and battery circuit 60. The housing 38 surrounds and protects the microprocessors 52 and circuits 54, 56, 58, and 60. The circuit diagrams/configurations of the microprocessor 52 and circuits 54, 56, 58, and 60 are shown in FIGS. 4-7F. As discussed above, other sensors such as, but not limited to, the temperature sensor may be incorporated into or onto the control unit 22. Further, it is appreciated by one skilled in the art that other circuitry may also be included in the control unit 22, depending on the vital data being obtained, and is not limited to pulse oximeter, ECG, and temperature circuitry as shown in FIGS. 4 and 7A-7F. Each circuit associated with a sensor input includes a separate channel for receiving the sensor data and communicating with the microprocessor. In a further embodiment, more than three channels are provided to allow for additional sensor data from additional sensors.

As shown in greater detail in FIG. 7A, the microprocessor 52 may have one or more wireless, wired, or any combination thereof of communication ports to communicate with external resources as well as various input and output (I/O) ports. For instance, input ports 90 for receiving output signals from the pulse oximetry, ECG, and temperature circuits, and outputs for any LED's used as indicator lights. The microprocessor 52 may be equipped with a BLUETOOTH® communication protocol chip 53, such as a BLE chip. However, in an alternative aspect, the microprocessor may be equipped with and utilizes other wireless communication protocols. The microprocessor may include hardware or software control logic to enable management of the microprocessor 52 including, but not limited to, converting the signals indicative of vital data from analog to digital signals for output to the vital monitoring application. The converted signals can be transmitted to the vital monitoring application 14 through the BLE chip 53. The microprocessor 52 may also have any combination of memory storage such as random-access memory (RAM), read-only memory (ROM), erasable programmable read-only memory (EPROM), or electrically erasable programmable read-only memory (EEPROM) 55.

Each of the circuits 54, 56, 58, and 60 are electrically connected or are in communication with various input ports of the microprocessor 54. Additionally, the pulse oximetry circuit 54 and ECG circuit 56 are electrically connected to its corresponding sensing devices.

With respect to the pulse oximetry show in FIG. 7B, the pulse oximetry circuit 54 receives a signal indicative (in analog form) of vital data relating to the oxygen saturation within the individual's blood. The pulse oximetry circuit 54 includes a two-part circuit which has a first part 62 that employs two light emitting diodes (LEDs) 64, 66 and a second part 68 that includes a photodiode 70, an amplifier 72, and a combination of capacitors and resistor 74. The circuit includes LEDs 64, 66 of the first part 62 face a photodiode 70 of the second part 68 and a space 76 is formed there between such that the individual's finger 78 fits within the space 76. In determining the individual's pulse oximetry levels, the light from the LEDs 64, 66, are projected onto a part of the of the body, usually a fingertip or earlobe, or in the case of an infant across the feet and the amount of light transmitted through the individual's body is measured. Alternatively, light reflected on the body may be used instead of light transmitted. In determining this different types of LEDs 64, 66 are provided. In one example, one of the LEDs 64 is a red LED with a wavelength of 660 nm and the other LED 66 is an infrared LED with a wavelength of 940 nm. Accordingly, the absorption of light at these wavelengths is different between blood loaded with oxygen and blood lacking oxygen. In particular, oxygenated hemoglobin absorbs more infrared light and allows more red light to pass through while deoxygenated hemoglobin allows more infrared light to pass through and absorbs more red light. In operation, the LEDs 64, 66 are powered by and sequenced using an LED driver circuit 80 that turns one LED ON, then the other LED ON, and then both OFF for a predetermined period of time, such as twenty times per second or 20 HZ. For example, the red LED is ON while the IR LED is OFF, then the red LED is OFF while the IR LED is ON, and then both LEDs 64, 66 are ON. The amount of light transmitted by the LEDs 64, 66 that is not absorbed is measured and converted into a signal (current) by the photodiode 70 to produce an output signal indicative of data relating to the level of oxygen in the individual's blood. In one example, the LEDS 64, 66 and the photodiode 70 can be located in a pulse oximeter box or a finger band and the rest of the circuit shown in FIG. 7B is located in control unit 22. The output signal is amplified and filtered through the second part 68 of the pulse oximetry circuit 54. The output 82 of the circuit 62 and 68 is in communication with an input of the microprocessor 52 and transmits the output signal there between. The output signal is converted into a digital signal in the microprocessor 52 and will eventually be transmitted to the application 14, shown in FIGS. 8A-8E, through BLE communication or the like.

Figure 7C:
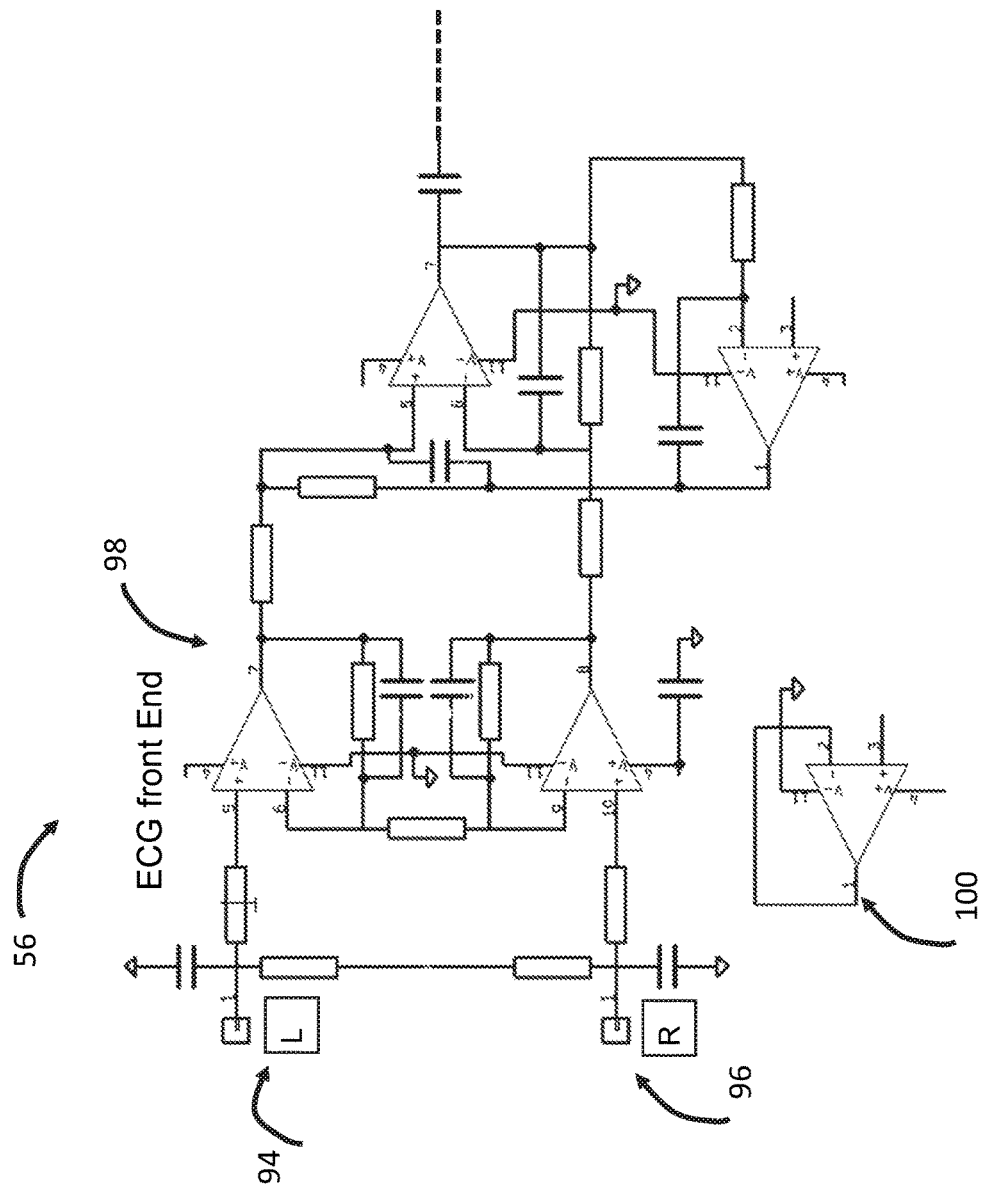
FIGS. 7C and 7D show a circuit diagram for an ECG sensor for a control unit of a portable vital monitoring device in accordance with an aspect of the present disclosure.
Figure 7D:
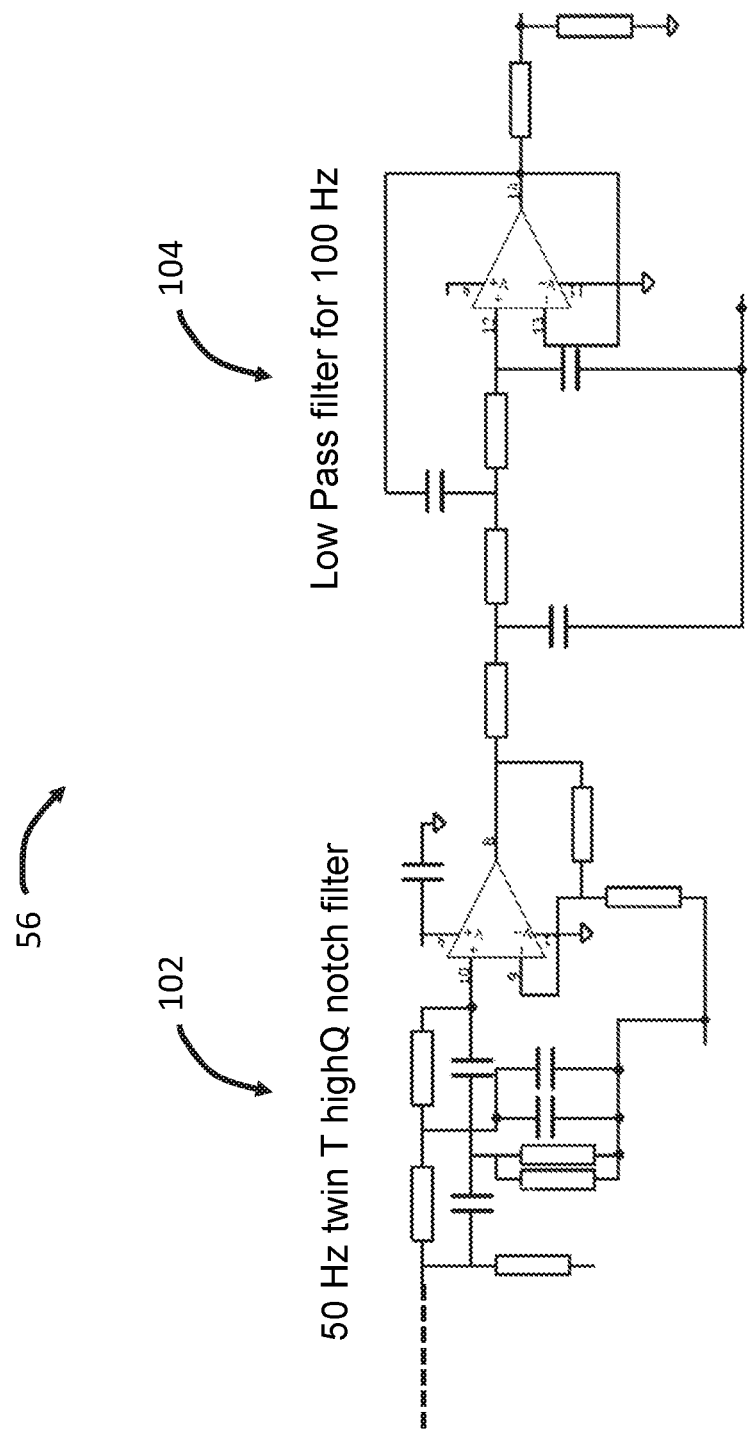

FIGS. 7C and 7D show an example circuit schematic of the ECG circuit 56 in accordance with an aspect of the present disclosure. The ECG circuit 56 has two inputs 94, 96 for receiving analog signals indicative of vital data relating to the electrical activity in the individual's heart from two electrodes. The ECG circuit 56 also has an ECG front end portion 98 for amplifying the analog signals consisting of a plurality of amplifiers, and a series of capacitors and resistors and an offset correction portion 100 for correcting the voltage of output signal and consisting of a plurality of amplifiers and a series of capacitors and resistors. In one example, a 50 Hz twin T highQ notch filter 102 for removing a single frequency from the signal is also present. The notch filter 102 rejects a single band of frequencies and allows all other frequencies to pass through the filter. The ECG circuit 56 further includes a low pass filter 104 for removing frequencies above a cutoff frequency. Accordingly, an output signal is generated and received by an input of the microprocessor 54, shown in FIG. 7A and is eventually transmitted to the application 14, as shown in FIGS. 8A-8E.

Figure 7E:
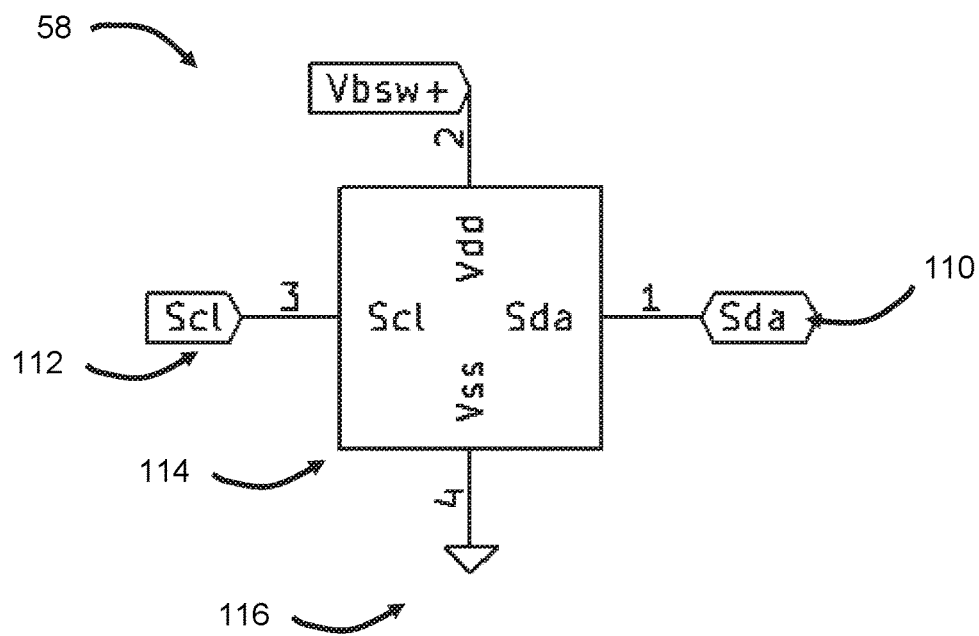
FIG. 7E shows a circuit diagram for a temperature sensor for a control unit of a portable vital monitoring device in accordance with an aspect of the present disclosure.
Figure 7F:
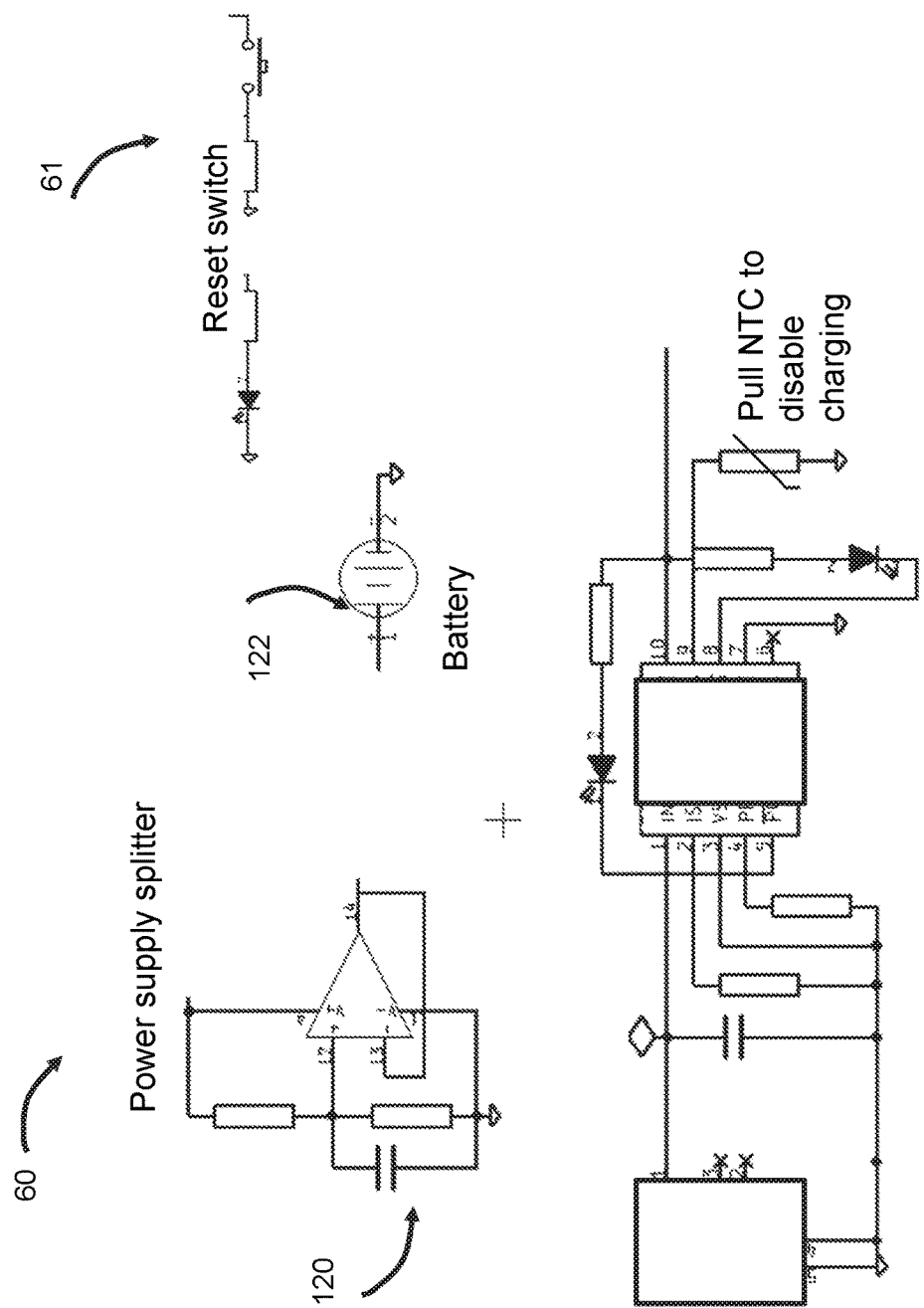
FIG. 7F shows a circuit diagram for a power configuration for a control unit of a portable vital monitoring device in accordance with an aspect of the present disclosure.

A temperature circuit 58 is shown in FIG. 7E. The temperature circuit 58 includes a serial data (SDA) 110, a serial clock (SCL) 112, a ground 116 for adjusting signal levels, an infrared thermometer 114 for temperature sensing and transmitting the signal indicative of data relating to skin temperature to the microprocessor 54. FIG. 7F shows a power supply and battery circuit 60 and a switch circuit 61, which includes a power supply splitter 120 for allowing a defined amount of power to be used in ECG circuit 56 and a battery holder 122 for receiving a battery (e.g., 3V cell battery) to power the control unit 22. The switch circuit 61 is utilized to power OFF and/or reset the device for enhanced power saving. Additionally, while not explicitly discussed above, each circuit shown in FIGS. 7A-7F includes one or more ground elements for providing a common turn path for electric current.

Again, it is appreciated by one skilled in the art that the circuitry discussed above is not limiting and may include, or may be adjusted to include, circuitry for different vitals or measurements in addition to ECG, pulse oximeter, and skin temperature.

FIGS. 8A-8F are examples of illustrations of multiple graphical user interfaces of a vital monitoring application 14, accessible via a smart device, for monitoring, processing, storing, and/or storing an individual's vitals in accordance with an aspect of the present disclosure. As discussed above, the portable vital monitoring system 10 includes a vital monitoring application 14 that communicates with the vital monitoring device 12 via BLE communication protocol or the like and receives one or more digital signals indicative of the individual's vital data. The application 14 is designed to and is programmed with software control logic to analyze the digital signals of vital data and display the vital data in graphical and/or numeric form on a smart device for view by a user, such as the individual, third-party caregiver, medical professional, or a third party located in a remote location. The application 14 is compatible and is downloadable on any smart device, such as a smart phone, smart watch, tablet, computer, laptop, or the like. The application 14 may be stored in memory of the smart device and accessed through an icon on the display of the smart device.

The application 14 is also operable to communicate with a remote server through an internet, broadband, and/or data communication, as described previously. The communications between the application and the server can be encrypted or made secure such that another user of the application 14 cannot access the individual's vital data without their permission.

Figure 8A:
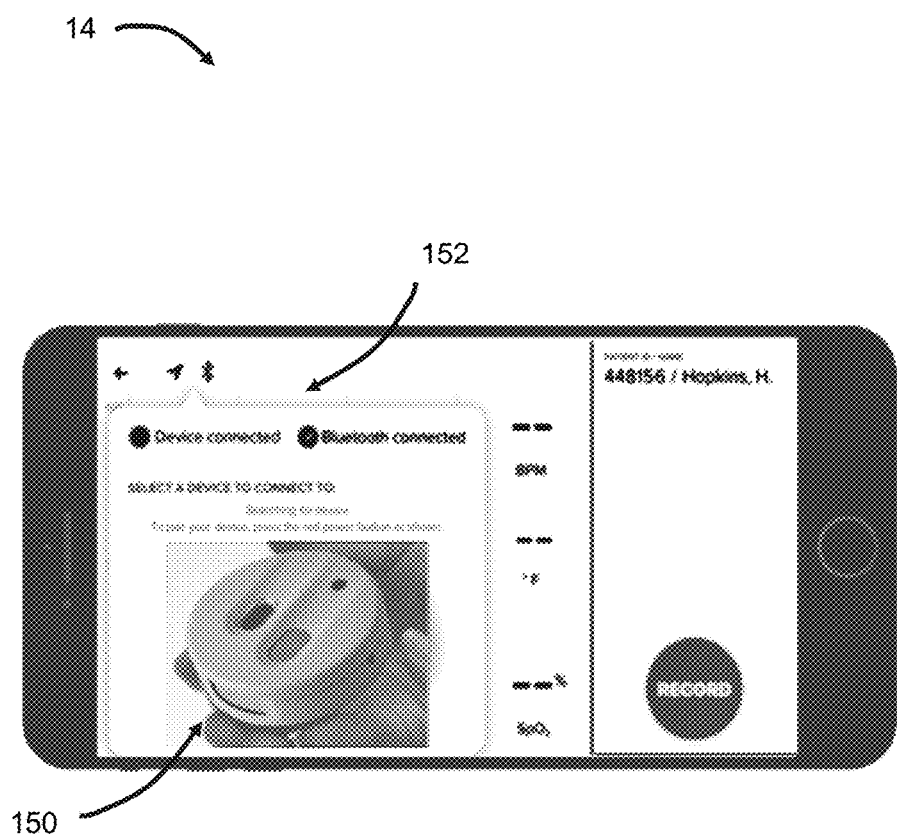
FIGS. 8A-8E are examples of illustrations for various graphical user interfaces of an application for monitoring an individual's vitals in accordance with an aspect of the present disclosure where

The application 14 may have various graphical user interfaces, as shown in FIGS. 8A-8F, to operate the application 14 and review the vital data obtained by a stand-alone vital monitoring device. In an example, the graphical user interfaces may include a scanning interface 150 as shown in FIG. 8A. The scanning interface 150 includes a scan button 152 that when engaged searches for the stand-alone vital monitoring device via BLE communication protocol to connect the device to the application 14. Specifically, the application 14 uses the BLUETOOTH®-communication protocol on the smart device to detect the BLE chip in the control unit of the vital monitoring device to connect the application 14 and vital monitoring device for transmitting data there between. It will be appreciated by one skilled in the art that other wireless communication protocols known in the art may be used as an alternative to BLUETOOTH®. Once the application 14 and vital monitoring device are connected, one or more signals indicative of the individual's vital data can be transmitted in real-time continuously or over a predetermined period of time.

In an example when application 14 and vital monitoring device are connected, a main display interface 154 is provided, where the user can view a list 156 of each vital 158 measured by the vital monitoring device. The list 156 may include the type of vital 158 such as ECG, pulse IR, and temperature with an associated numerical or graphical representation of the measurement obtained from the individual. Each type of vital 158 on the main display interface 154 may be a button that when selected displays graphical interface that shows the selected vital data in a graph form. For example, if a medical profession selects an ECG button on the main display interface 154 in FIG. 8B, then the application 14 will display the graph interface 162 showing a graphical representation of the individual's heart activity, as shown in FIG. 8C.

Figure 8B:
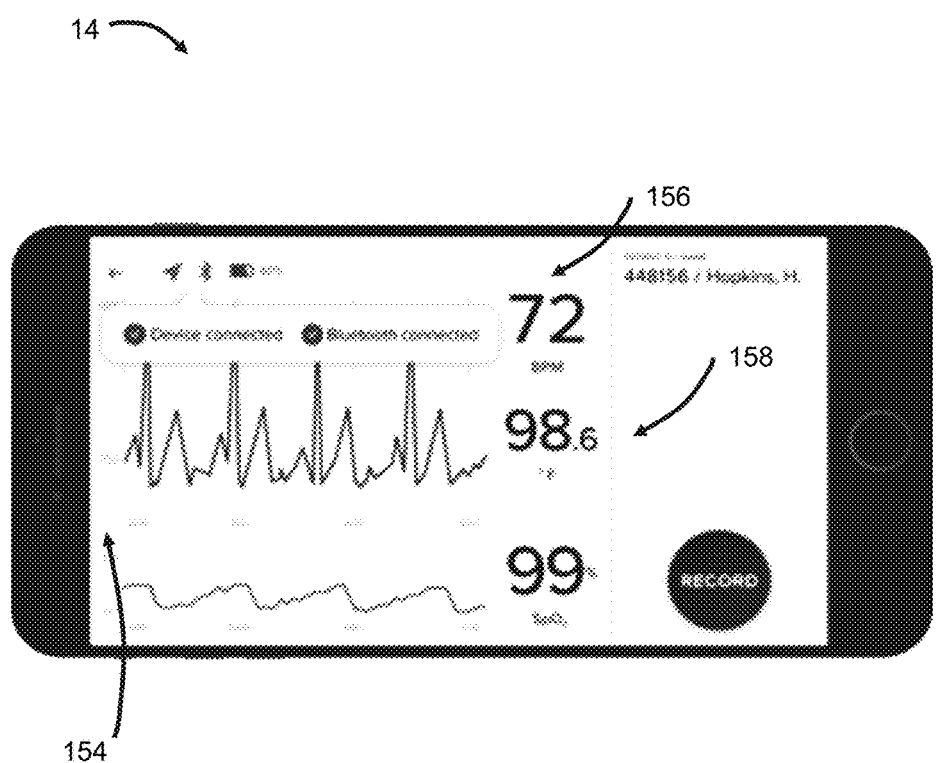
Figure 8C:
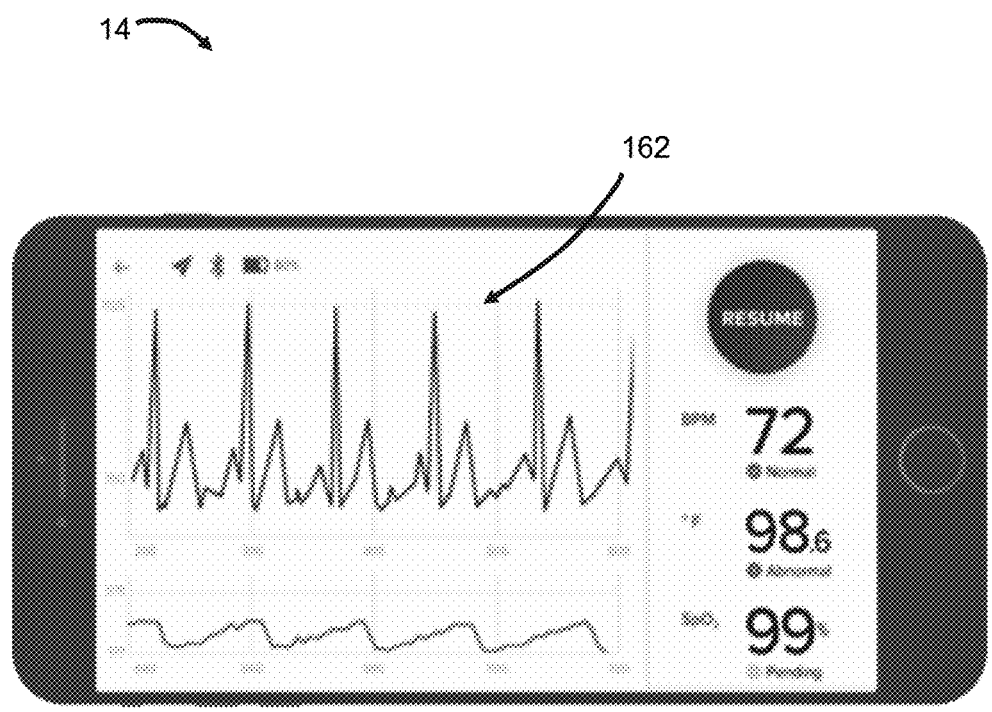
Figure 8D:
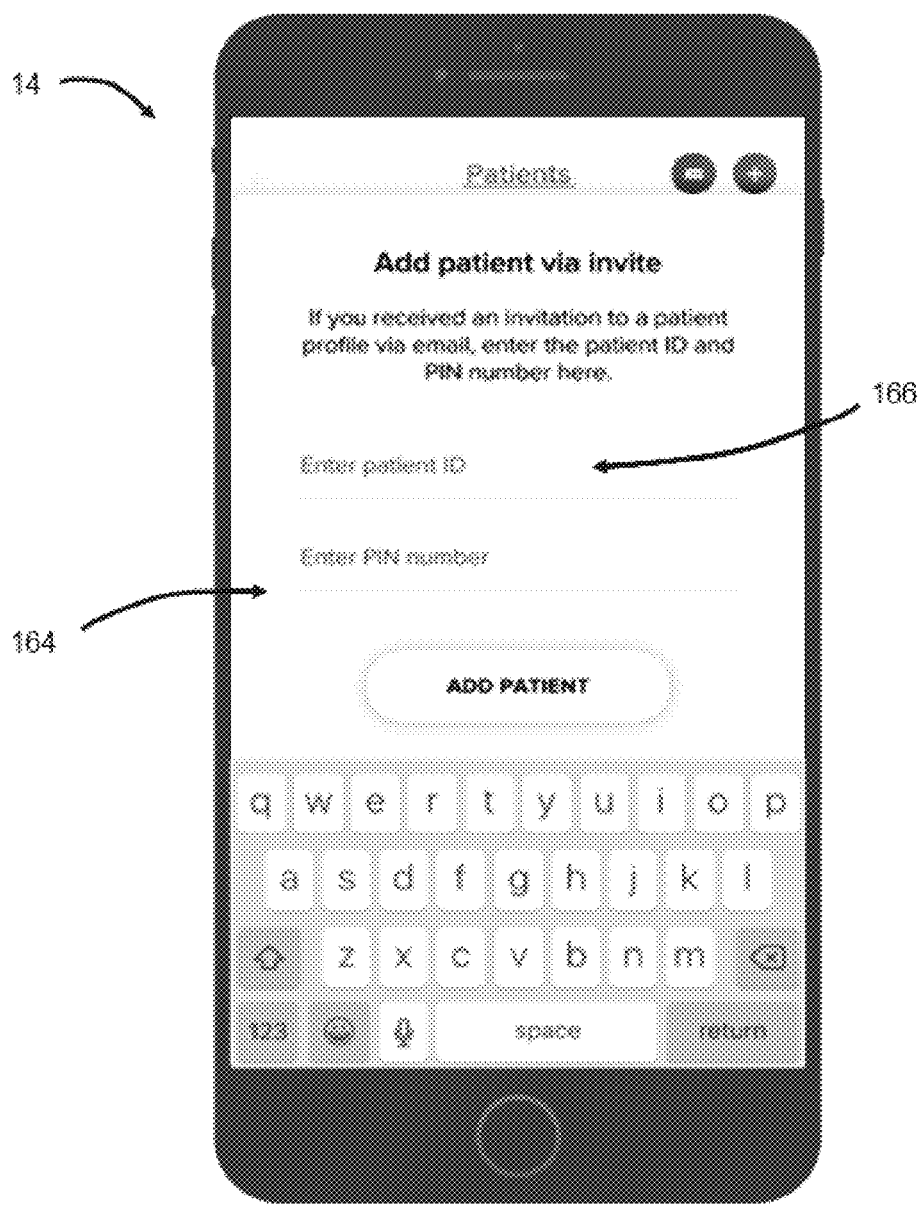

In another aspect of the present disclosure, as disclosed in FIG. 8D, the application 14 may have a patient identification (ID) interface 164, where the user would enter a patient's identification (ID) number 166 associated with the individual to access their vital data. The ID interface 164 may be used in multiple settings. For instance, if a doctor is taking the individual's vitals in a hospital setting, the doctor can use the portable vital monitoring device to obtain the vital data and then use a smart device, such as a smart phone or tablet, to view the results after they have entered the individual's patient ID number. In another instance, a third party located at a remote location from the individual may have access and can view the individual's vital data after they have entered the patient ID number.

Figure 8E:
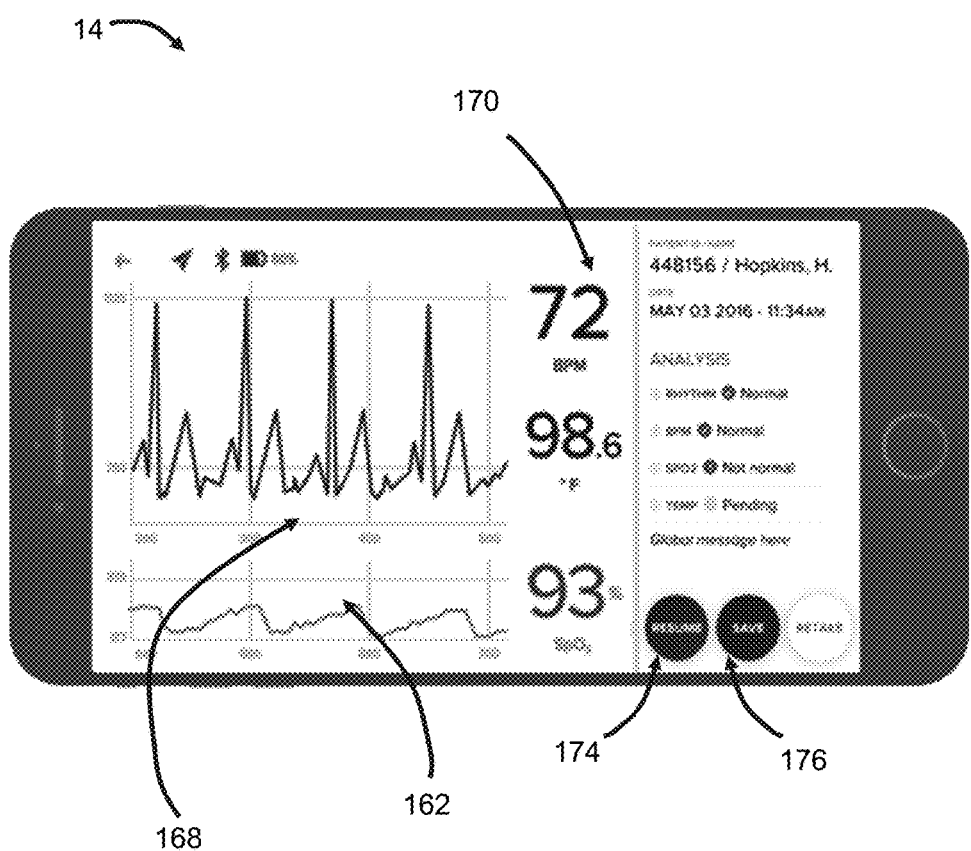
Figure 8F:
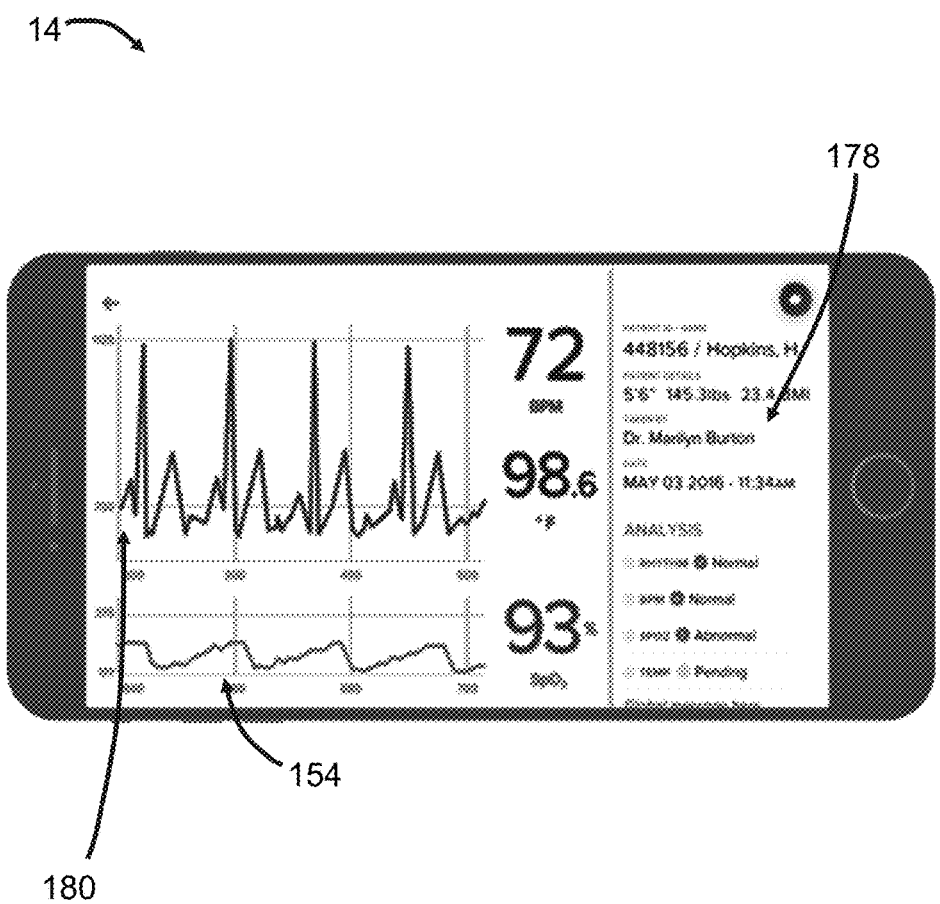
FIG. 8F shows another patient main display interface.

Once the patient ID number is entered, interfaces (FIGS. 8E and 8F) similar to the interfaces shown in FIGS. 8B and 8C can be viewed. In particular, FIG. 8E shows another example of a graphical interface 162 with a graphical representation 168 of the vital data, a numerical representation 170 of the vital data, a pause/resume button 174 for reviewing a particular portion of the vital data, and a save button 176 for storing and uploading the vital data to a server. Similarly, FIG. 8F shows another example of a main display interface 154, which includes individual or patient details 178 and identifying information such as their age, gender, height, and weight, as well as a history 180 of their past vital data. As such, the user will be able to view the individual's vital data in real-time as well as have access to view their past vital data for determining treatment and for detecting any anomalies or changes in their vital data. The application 14 may also display an alert when an anomaly or change in vital data is detected.

It will be readily appreciated by one skilled in the art that various other interfaces of the application 14 are within the scope of the present application. Accordingly, there may also be a registration interface where the user provides identifying information to register and log-in to the application 14. In one example, only the user registered will be able to view the vital data displayed on the application 14. If a medical professional or a third party is registered to the application 14, then they may have access to the individual's vital data after the individual authorizes them to view the data.

Figure 9:
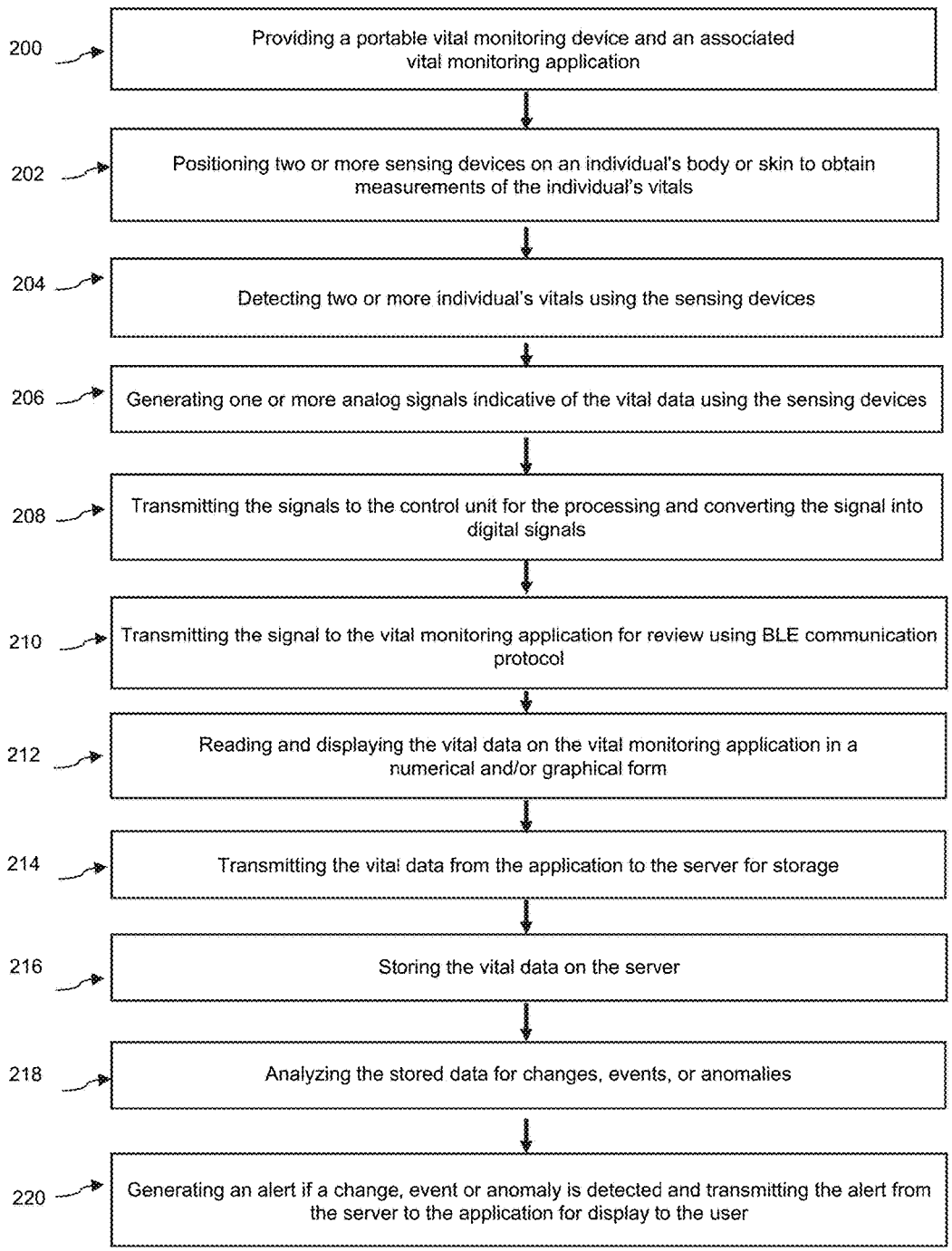
FIG. 9 is a flowchart of a method for monitoring an individual's vitals using a portable vital monitoring system in accordance with an aspect of the present disclosure.

FIG. 9 is a flowchart of a method for monitoring an individual's vitals using a portable vital monitoring system in accordance with an aspect of the present disclosure. The portable vital monitoring system includes the same components described above in FIGS. 1-6E. The method includes providing a portable vital monitoring device and an associated vital monitoring application 200 and positioning two or more sensing devices on an individual's body or skin to obtain measurements of two or more of the individual's vitals 202. For example, two wristbands each equipped with an electrode are placed around the individual's wrist, and the individual's finger is inserted in a finger band or a pulse oximeter box. The sensing devices then detect or measure the individual's vitals 204 and generate one or more analog signals indicative of the vital data 206.

The signals are transmitted to the control unit where they are processed and converted from analog signals into digital signals 208. Processing may include amplifying and filtering the signal. Once the signals are converted into a digital signal 208, the control unit may transmit the signals to the vital monitoring application for review using BLE communication protocol or the like 210. The vital data is read and displayed on the vital monitoring application in a numerical and/or graphical form 212.

The method may further include transmitting the vital data from the application to the server for storage 214 and storing the vital data on the server 216. The server can analyze the stored data for changes or anomalies in the vital data 218. If a change or anomaly is detected 218, then the server can generate an alert and transmit the alert to the application for display to the user 220.

Referring to FIGS. 10A-10D, another example of a dedicated vital monitoring system and device is shown. Device 300 is a stand-alone, dedicated vital monitoring device and includes a housing 302 which can also be referred to as a case or casing 302 for enclosing internal components such as a circuit board, microprocessor, and a plurality of sensors. In this example, housing 302 defines a circular geometry forming a disc-like structure having a thickness extending from a face 304 to a back side 306. A side portion 305 extends around a perimeter of the circular face 304 and back side 306 forming the enclosure. In one example, the device 300 forms a cylindrical disk having a diameter of about 55 mm and a height of about 20 mm.

Figure 10A:
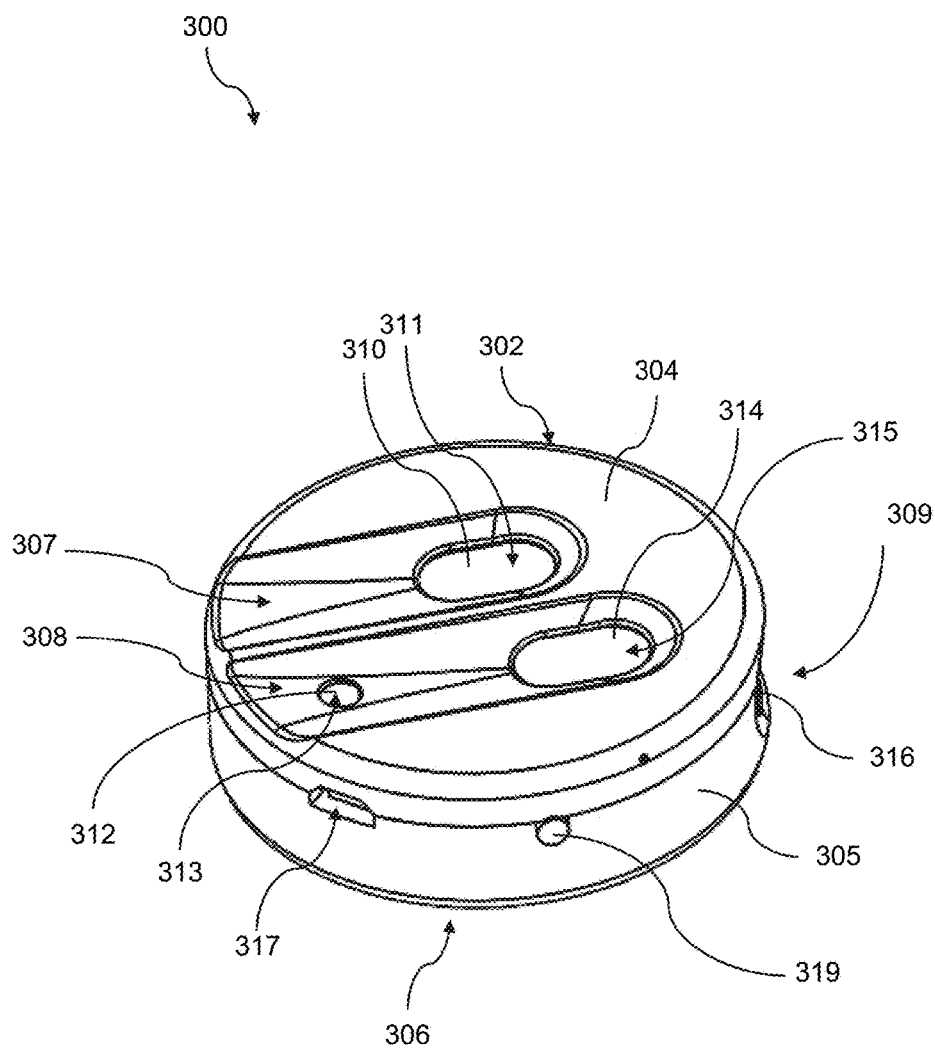
FIGS. 10A-10D illustrate an example dedicated vital monitoring device according to the present disclosure where
Figure 10B:
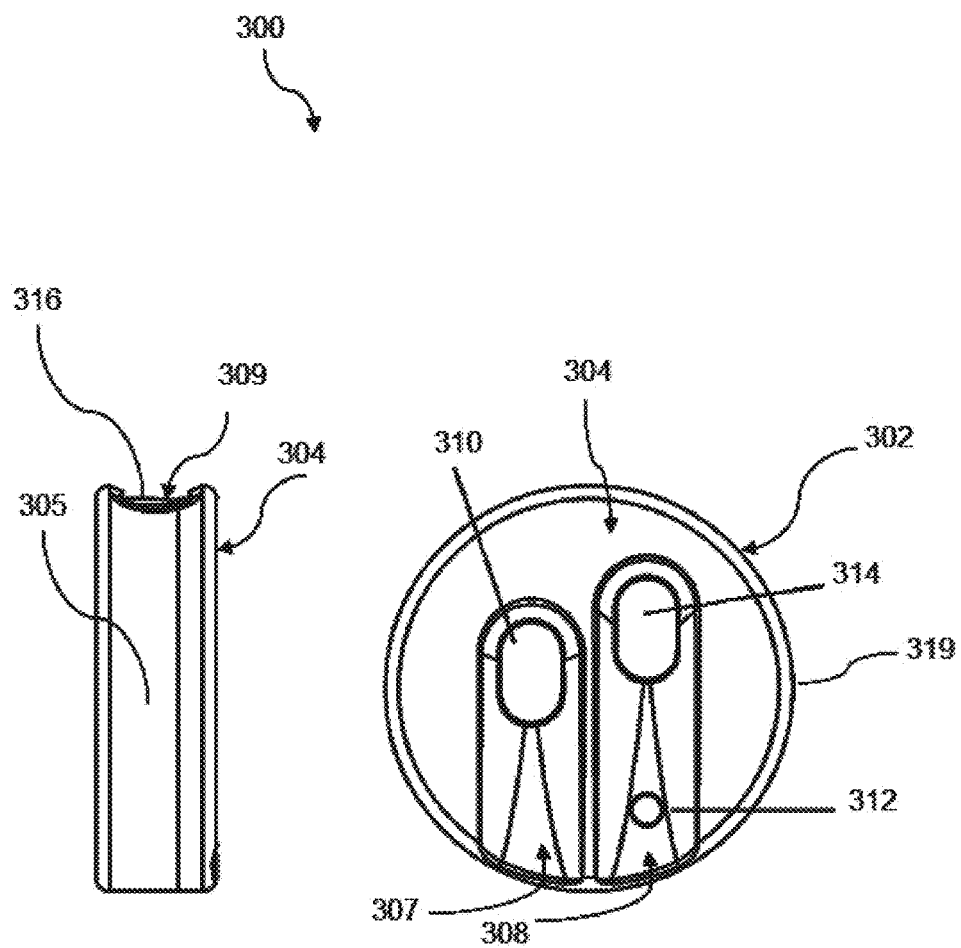
Figure 10C:
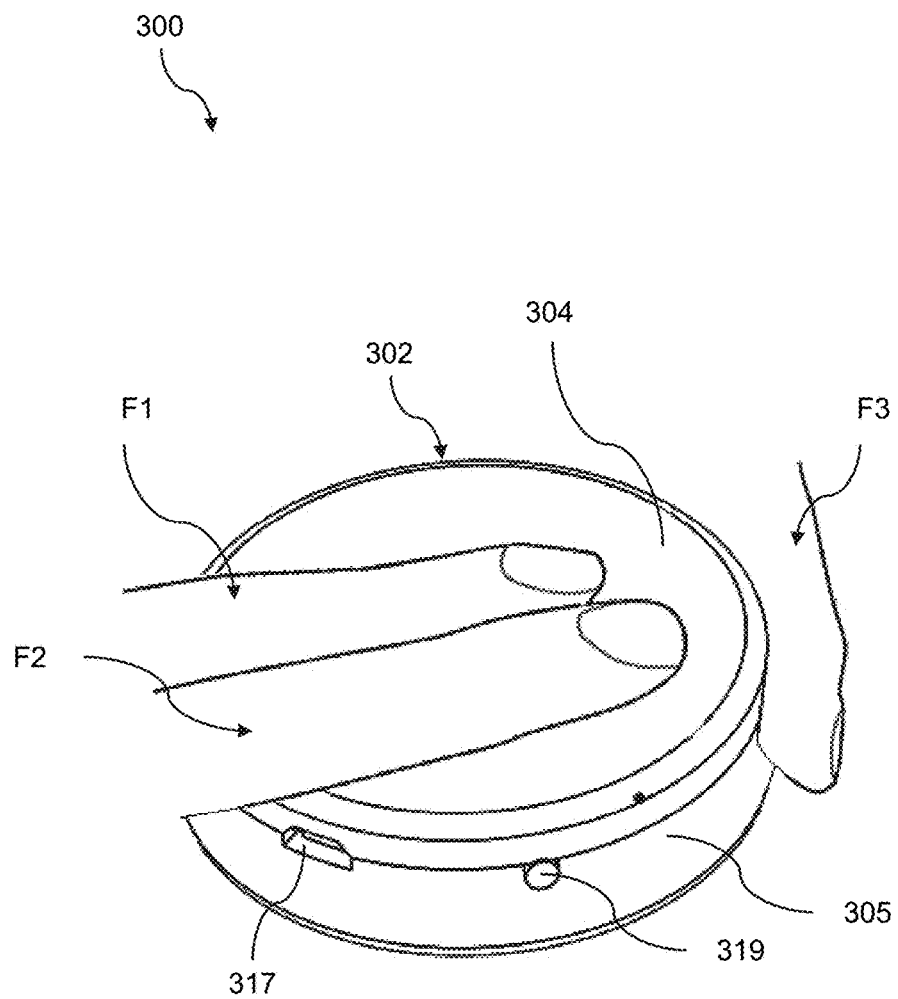
Figure 10D:
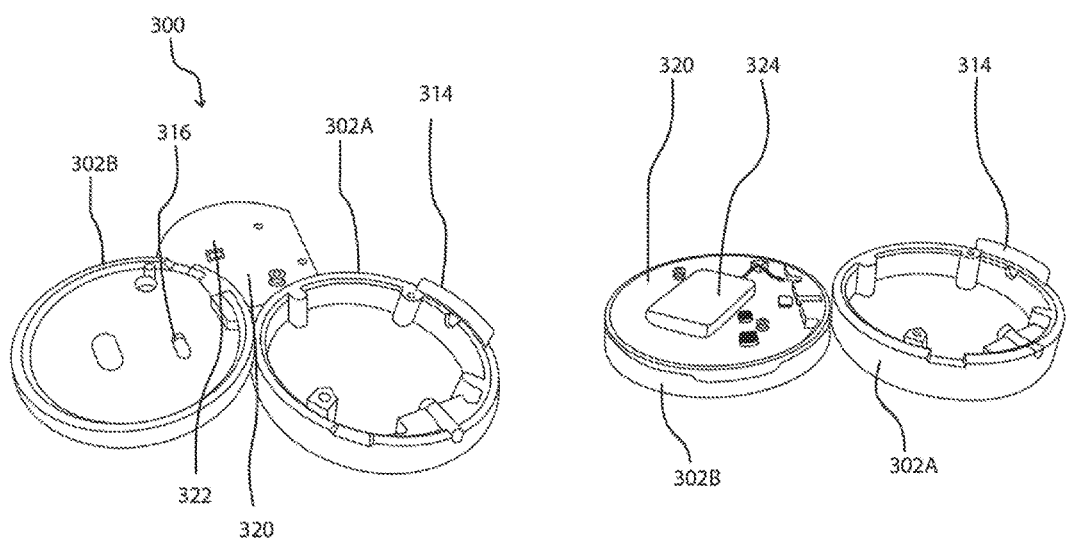

In this example, the face 304 defines a pair of sensor sections shown as first finger depression 307 and second finger depression 308 sized and shaped to receive two fingers from a user as shown in FIG. 10C. First finger depression 307 is a pulse oximetry finger depression having a pulse oximetry sensor 310 provided therein. Pulse oximetry sensor 310 is provided within the housing 302 and exposed through an opening 311 defined in the first depression 307. In this example, a lightguide window is provided to allow operability of the sensor 310 to transmit and receive signals that engage with a first finger F1 of a user. Second finger depression 308 is sized and shaped to receive a different finger from the user. A temperature sensor 312 is disposed within the depression and operable to measure skin temperature of the user. The position of the temperature sensor 312 within second depression 308 can be selected according to a sufficient location for adequate physical contact with the skin of the user. Temperature sensor 312 is accessible through an opening 313 formed on second finger depression 308. A lightguide window can also be provided in opening 313 to allow temperature sensor 312 to engage with a second finger F2 of a user. Temperature sensor 312 can be a contactless temperature sensor.

Positioned further into the second finger depression 308 is a first electrode 314 operable to contact a second finger F2 of the user. First electrode 314 is accessible through an opening 315 formed on a surface of the second finger depression 308. The first electrode 314 works with a second electrode 316 positioned on side portion 305. In this example, the second electrode 316 is provided in a third finger depression 309. Finger depression 309 is sized and shaped to receive a finger of the user from an opposite hand from the fingers used in the first and second finger depressions 307 and 308. First and second electrodes 314 and 316 are coupled to an interior circuit board 320 and a microprocessor 322. First and second electrodes 314 and 316 can be silver electrodes.

The microprocessor 322 can obtain signals form the sensors associated with vital data of the user, process that data, and communicate through a communication module or protocol with a remote server and/or a mobile device and/or a mobile application. The data can be further be stored and processed by the microprocessor 322. In a further embodiment, the processed data can be included into a machine learning algorithm to study user vital history. The machine learning can then provide real time or near real time alerts and notifications to a user associated with vitals. In yet another embodiment, data is transmitted to a mobile application which is hosted on a mobile device through a wireless communication protocol or module. The data is then processed and converted into information to be displayed through a graphical user interface on the mobile device through the mobile application as shown in FIGS. 8A-8F.

Device 300 can include similar components as discussed with respect to the flow diagram of FIGS. 1-2. Accordingly, a device 300 can be comparable in term of function as the control unit 22 and can include a power source 24 coupled to the circuit board of the control unit. The power source can a battery sufficient to power the device 300. In a further example, the power source includes a rechargeable battery. Device 300 can include a switch 313 coupled to the power source for turning the device on and off. In this example, switch 313 is positioned on the side portion 305. A charge port 315 can be provided to allow recharging of the power source. In this example, the charge port is a micro USB port operable to engage a micro USB charger cord and plug.

In one example, the circuit board 320 can include a mother board connected to a battery such as a Lithium Polymer (Li—Po) battery 324. The housing 302 is constructed of two parts, a top 302A and a bottom part 302B that are connected along a perimeter. The housing 302 can be constructed to allow access to the internal components such as circuit board 320, microprocessor 322, battery 324 and any of the sensors and/or electrodes. The ECG electrodes 314 and 316, pulse oximetry sensor 310, and temperature sensor 312 are accessible on the surface of the housing 302 and electronically coupled to the circuit board 320. The microprocessor 322 serves as the control unit and is mounted on the motherboard 320. In one example, the control unit is operable to amplify, filter, digitize and wirelessly transmit the received signals from sensors. Battery 323 can be any battery including a 3.7 V, 300 mAh Li—Po battery.

Figure 11:
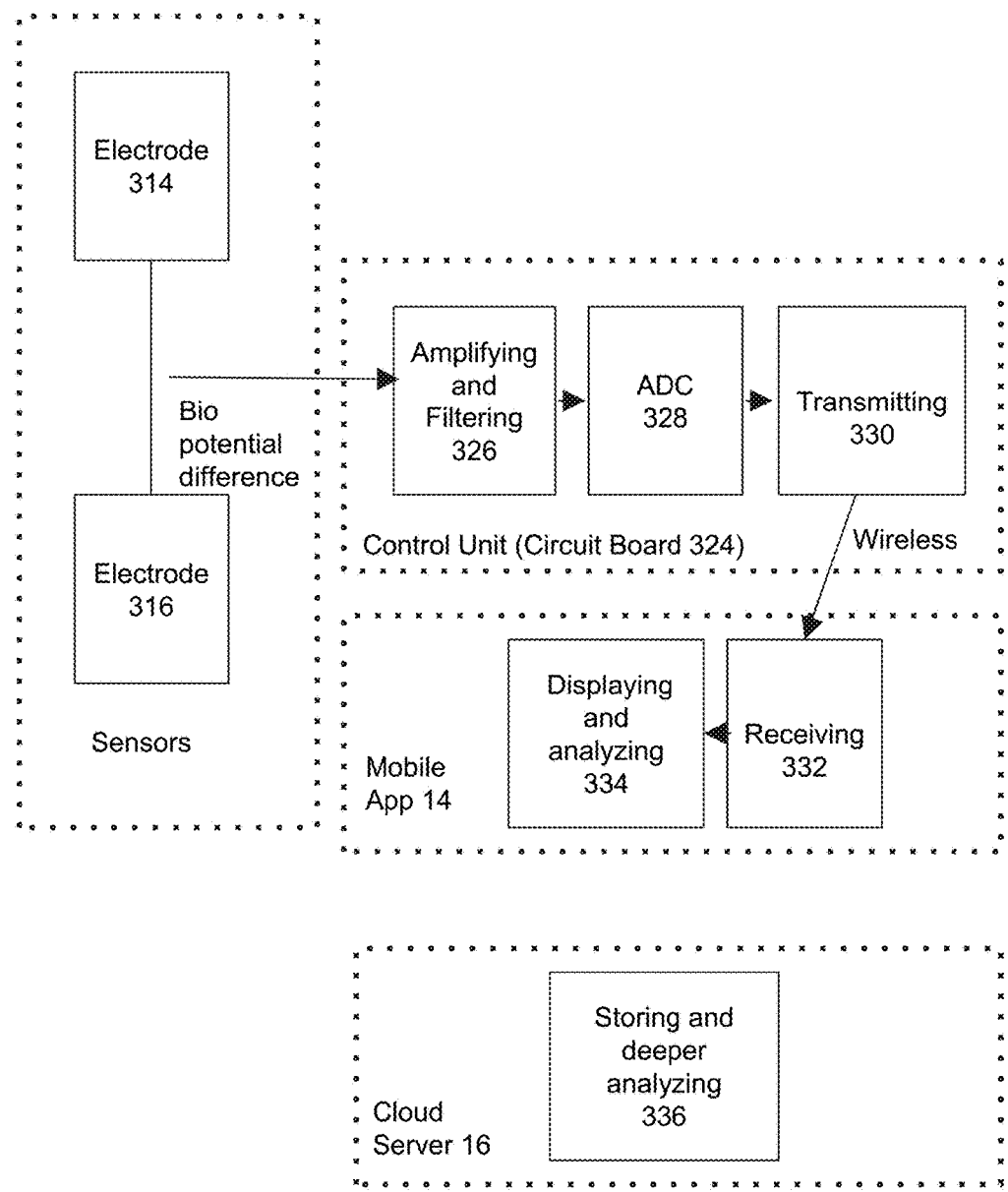
FIG. 11 a block diagram of a portable vital monitoring system in accordance with an aspect of the present disclosure for obtaining and transmitting ECG vital information.

FIG. 11 illustrates a flow diagram of the example device 300 in use for determining ECG data using a mobile application 14 and remote and/or cloud server 16. ECG is the process of the electrical activity of the heart over a period of time. Electrodes, such as first and second electrodes 314 and 316, are placed on the skin to detect the electrical changes that arise from the heart muscle's electrophysiologic pattern of depolarizing and repolarizing during each heartbeat. Device 300 allows for placing a user's fingers F2 and F3 on the electrodes 314 and 316 through the finger depressions 308 and 309. The voltage difference created generates a signal that is then sent to the through the circuit board 324 to be amplified and filtered (box 326). Then this analog signal is digitized (box 328) and transmitted via a wireless protocol such as BLUETOOTH (box 330). A mobile application 14 associated with device 300 can then receive this signal (box 332) and display information (box 334) graphically and numerically. In one example, calculations, such as heart rate and heart rhythm and analysis can be done at the mobile application itself using the received signals. When the reading is stored in the mobile application, it will be uploaded to the cloud server for future reference. Deeper analysis (box 336) such as machine learning to detect arrhythmias and comparing with other channels can be done on the server side as the data can also be transmitted to a remote server 16 which is in communication with the mobile application 14.

Example of device 300 in use includes the steps of turning device 300 on using the switch 319. Device 300 is then connected the mobile application 14. Next, a patient/user will place first finger F1 and second finger F2 (from the right hand) into the finger depressions 307 and 308 and covering pulse oximetry sensor 310, temperature sensor 312 and first electrode 314. Then the patient/user places a finger F3 from their left hand into the depression 309 and contacting electrode 316 located on side portion 305. An ECG waveform and heart rate will then be displayed on the mobile application graphical user interface. These readings can be uploaded to a remote cloud server for the future reference and sent to or accessed by a care giver if desired. A patient's heartrate vital can be calculated and/or approximated based on ECG data.

Figure 12A:
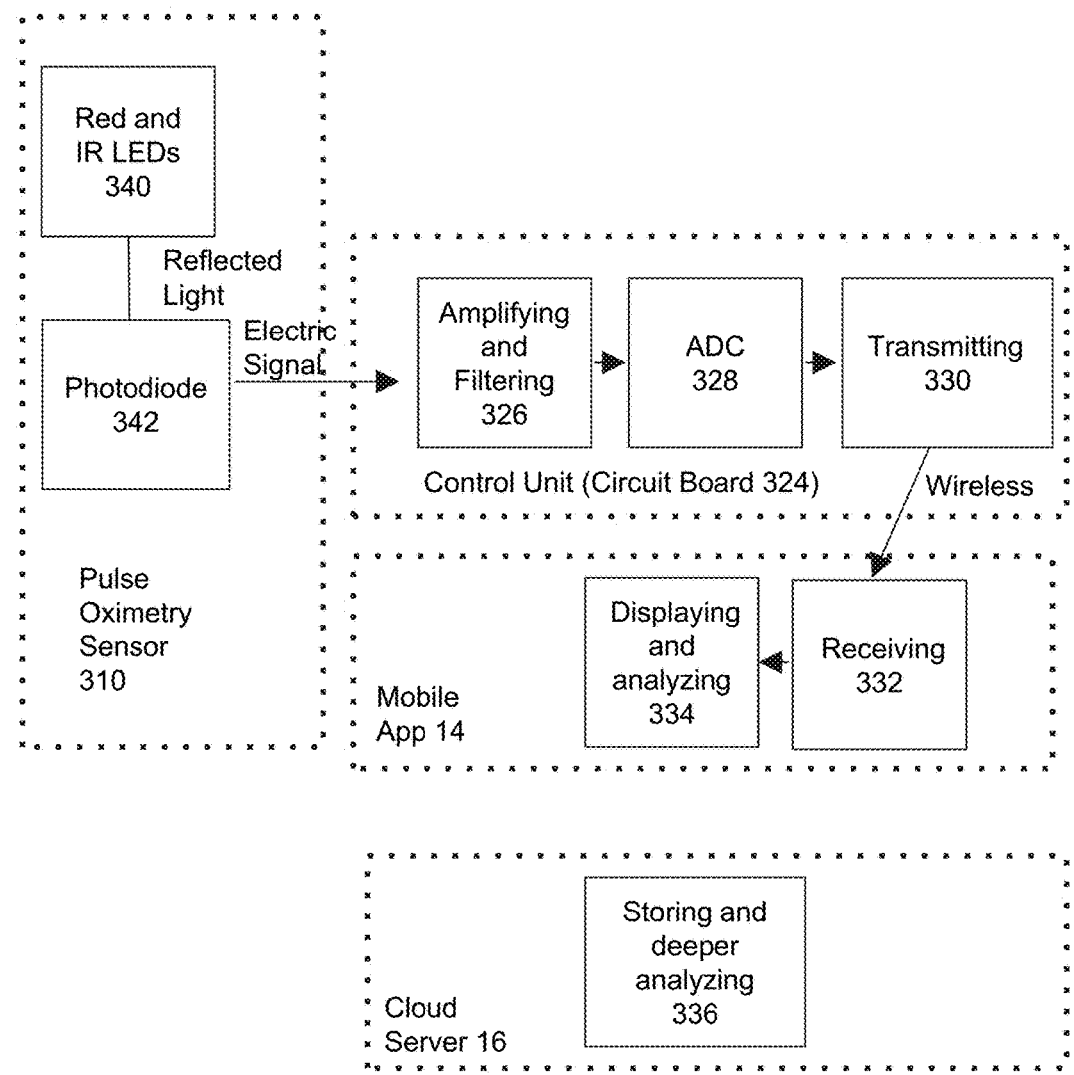
FIG. 12A a block diagram of a portable vital monitoring system in accordance with an aspect of the present disclosure for obtaining and transmitting pulse oximetry vital information.
Figure 12B:
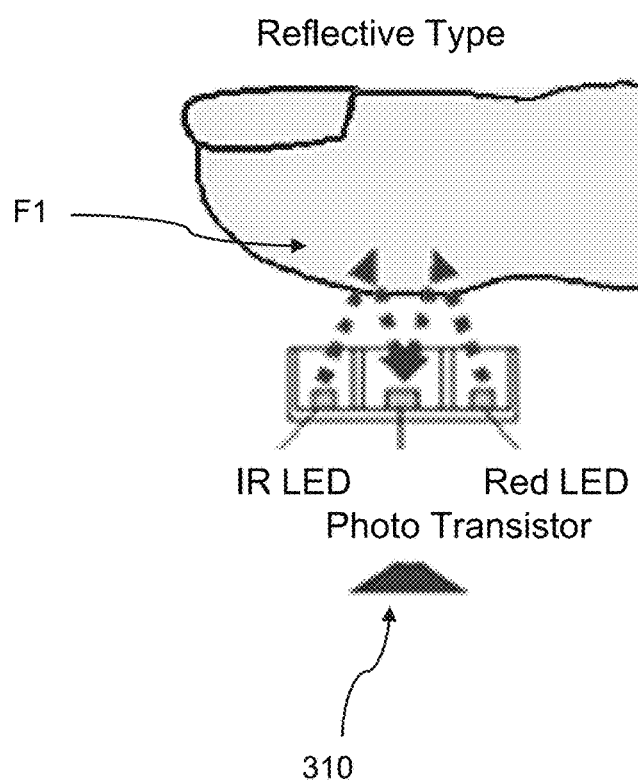
FIG. 12B is a schematic showing a pulse oximetry sensor in use with a finger of a user.

FIGS. 12A-12B illustrate a flow diagram of the example device 300 in use for determining pulse oximetry data using a mobile application 14 and cloud server 16 and use of a reflective type sensor 310. An important element needed to sustain life is oxygen (O2). The measurement and calculation of the percentage of Oxyhemoglobin (HbO2) in arterial blood is known as oxygen saturation. Depending on the measurement site, either a transmissive or a reflective mode can be used. In the transmissive mode, the light sources and photodiode are opposite to each other with the measurement site between them. In the reflective mode, the light sources and photodiode are positioned on the same side, and the light is reflected to the photodiode across the measurement site. Example device 300, according to the present disclosure, can use the reflective mode (shown in FIG. 12B) to increase the compliance of the device.

Device 300 allows for placing a user's fingers F1 on the sensor 310 in finger depression 307. This generates a signal that is then sent to the through the circuit board 324 to be amplified and filtered (box 326). Then this analog signal is digitized (box 328) and transmitted via a wireless protocol such as BLUETOOTH (box 330). A mobile application 14 associated with device 300 can then receive this signal (box 332) and display information (box 334) graphically and numerically. In one example, calculations and analysis can be done at the mobile application itself using the received signals. When the reading is stored in the mobile application, it will be uploaded to the cloud server for future reference. Deeper analysis (box 336) such as machine learning to detect arrhythmias and comparing with other channels can be done on the server side as the data can also be transmitted to a remote server 16 which is in communication with the mobile application 14.

Example of device 300 in use incudes the steps of turning device 300 on using the switch 319. Device 300 is then connected the mobile application 14. Next, a patient/user will place first finger F1 from the right hand into the finger depressions 307 and covering pulse oximetry sensor 310 which is exposed through a glass window. Pulse oximetry percentage (SpO2%) values and pulse waveform will be displayed on mobile application 14. Pulse rate can be calculated and be compared with heart rate from ECG (as described above) to ensure the accuracy. These readings can be uploaded to a remote cloud server 16 for the future reference and sent to or accessed by a care giver if desired.

In addition to ECG and SpO2 measurement, device 300 is further operable to take skin temperature measurement as well. In an example, an infrared temperature sensor 312 is used to measure the temperature. This sensor infers temperature from a portion of the thermal radiation emitted by the skin of a user without a direct contact. When finger F2 is placed over the temperature sensor 312, it measures the temperature and stores in memory as raw data. The microprocessor 322 reads the raw data and interprets in Fahrenheit. Temperature values can then be displayed numerically on the mobile application 14 and/or be stored in cloud server 16.

Measurement made by device 300 can be sent to a mobile platform application 14 via any wireless communication module or protocol. This can be an off-the-shelf component or built onto the circuit board 320. One example is using a BLUETOOTH or BLUETOOTH Low Energy protocol. The mobile application 14 will receive the data, do the calculations using an algorithm and display it numerically and graphically. When a user saves the data in the mobile application 14, it can be uploaded to remote server or cloud server 16 via internet (e.g., Cellular data or Wifi).

Example materials available for use in constructing a device 300 can be any materials suitable to achieve the desired results. Silver is a suitable material for the ECG electrodes. Various glass materials including acrylic glass are sufficient for a pulse oximetry window. The housing 302 can be constructed of most plastic materials including but not limited to polycarbonate or various combinations of polycarbonate such as polycarbonate+acrylonitrile butadiene styrene (PC+ABS). In one example, device 300 is provided in a pouch having a zipper for convenient user access.

In a further aspect of the vital monitoring system of the present disclosure, the system includes monitoring other activities associated with the user including but not limited to any physical activity, diet, habit/addiction related activities, sleep patterns, among others, and combinations thereof, and tracking those activities in the vital monitoring application. The system can then employ a machine learning algorithm that provides early intervention alerts for users by analyzing data coming from a combination of two or more channels, one or more vital sensors, and/or at least one of the activities described above.

The vital monitoring system of the present disclosure provides for a portable, compact, accessible, and cost effective solution to issues associated with current vital measuring options. The system also provides the ability to use a single device to measure or detect multiple types of an individual's vitals. Further, the system provides the ability to access and analyze the vital data easily and in real-time through a vital monitoring application, wirelessly transmit the vital data to a server, generate intervention alerts generated by machine learning algorithm using vital, physical, diet and habits/addiction data of the individual and access analyses from a remote location by authorized users and by the individual.

Another aspect of the vital monitoring system may include a machine learning algorithm operable to diagnose the issues from an ECG reading taken from a control unit or vital monitoring device 300. A list of example diagnosis that can be made using the system of the present disclosure include but not limited to: arrhythmia detection, hyperkalemia, hypercalcemia, Wolf-Parkinson-White syndrome, long QT syndrome, short QT syndrome, Torsades de Pointes, and others.

In yet another aspect of the vital monitoring system of the present disclosure includes providing a device with desirable comforting and soothing features. For example, the device 300 can be constructed with a light which illuminates and changes color to simultaneously sooth and calm patients and indicate progress of a reading. The light may change from red to purple or other colors that may be more culturally relevant. The light on the vital monitoring system may also pulse when a reading is complete, increasing and decreasing the light intensity to provide a soothing effect. In a further example, the device is formed with an outer shape and of a material comforting and soft to provide a more comforting stimulus to the user. The device may include an outer form that is soft, warm, and pliable to relieve stress and provide comfort. This reduces what may be a stressful experience of having vitals checked in stressful situations.

Figure 13:
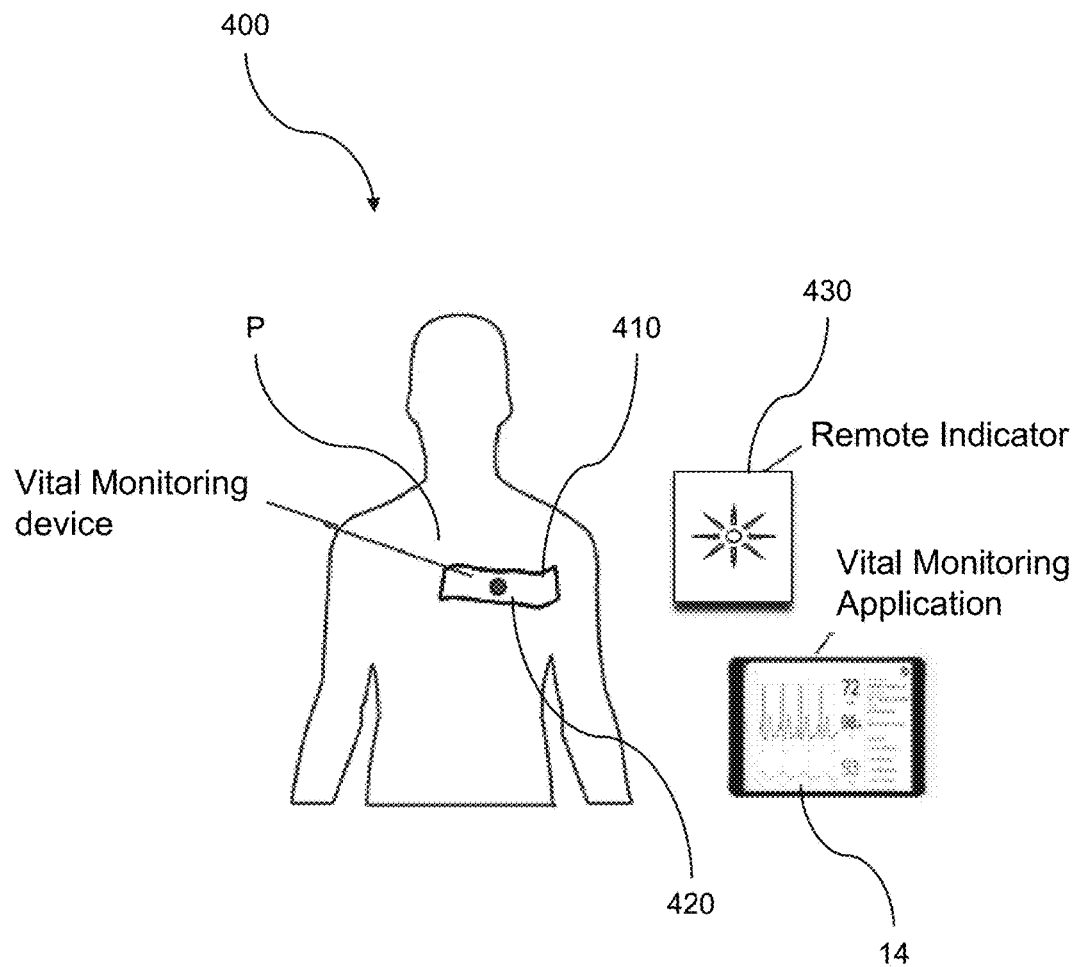
FIG. 13 illustrates a schematic for a personal and wearable vital monitoring system according to the present disclosure.
Figure 14:
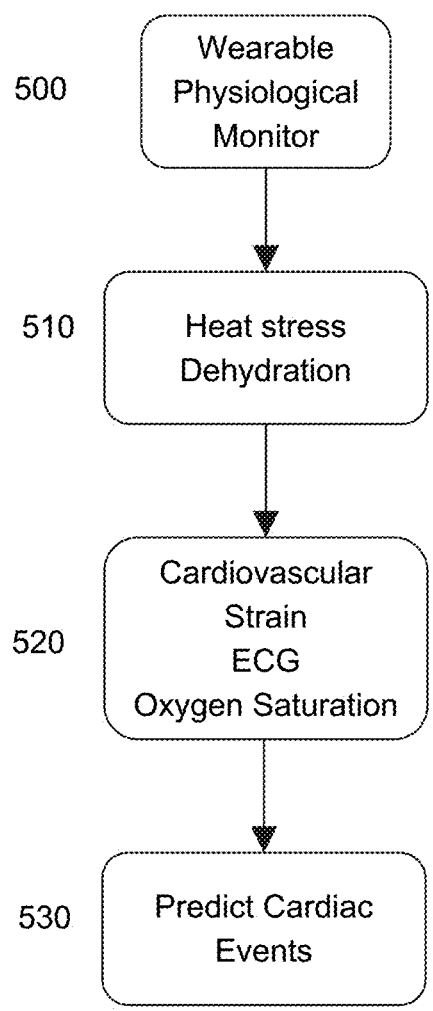
FIG. 14 is a block diagram of an example system of use of a wearable device according to the present disclosure.
Figure 15:
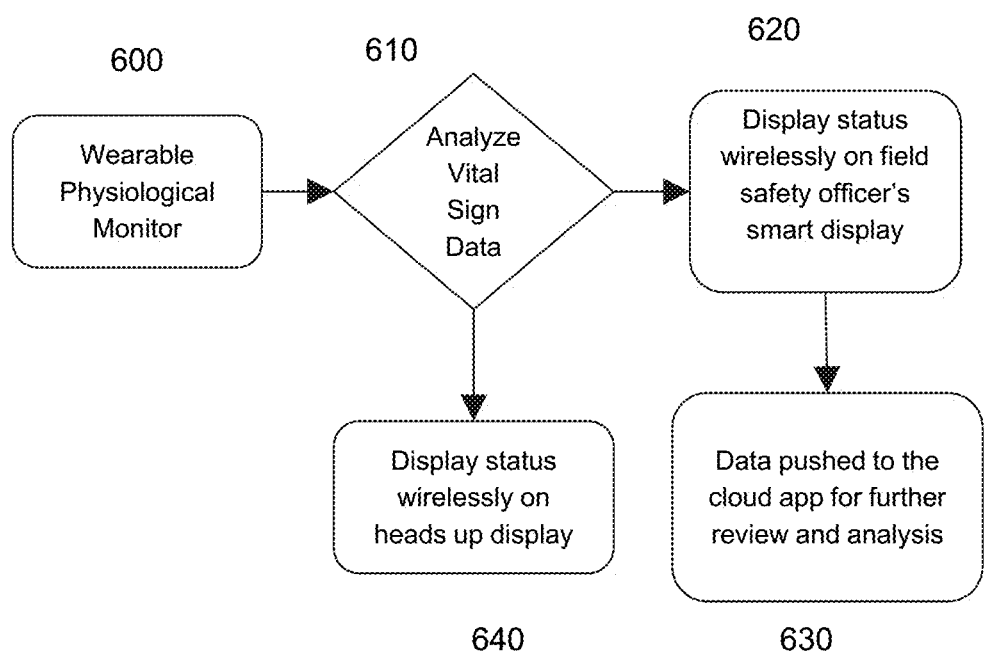
FIG. 15 is a further example of a block diagram of a system of use of a wearable device according to the present disclosure.

Referring to FIGS. 13-15, another example of the vital monitoring system of the present disclosure is provided. System 400 is shown having a wearable vital monitoring device 410. This device is sized and shaped to fit comfortably on a user. In this example, device 410 is placed near on a chest of a user P to be proximate the user's heart. Device 410 includes at least two sensing devices 420 operable for measuring the vitals of a user P. The sensing devices 420 are operable for obtaining vital information from the user P including at least ECG and skin temperature. In a further example, an ambient temperature sensor is included in device 410 to provide for risk management and monitoring by comparing changes to ambient temperature as it compares to skin temperature of the user P.

In another example, as shown in FIG. 13, a remote indicator 430 is used such as a light, buzzer, haptic or display that alerts the user in case of abnormalities in vital health or high risk situations. This feature may be helpful for users who work in extreme conditions when they cannot easily view the vital monitoring application on a corresponding smart device. The vital monitoring device 410 can be placed in proximity to the skin of a user P (Ex: at chest), an indicator 430 can be attached to anywhere the user P can see or hear or feel (Ex: Face mask, helmet, watch). When vital readings are abnormal, an indicator 430 will alert the user P through some sort of suitable stimulus such as physical, auditory, and/or visual. While the remote indicator 430 is giving an alert to the user P, vitals can simultaneously be monitored by the vital monitoring application 14 as well. For example, a fire fighter (user P) with a vital monitoring device 410 attached on the chest can get an alert 430 via light, buzzer, haptic or display when certain warning signs or risk factors are present via the monitoring of the user's vitals. So if the change in skin temperature gets too high, the vital monitoring application may send a warning signal to the user P that they are at higher risk of dehydration and thus heart complications. This allows for more accurate and real-time safety monitoring. The fire fighter's vitals can also be monitored by an onsite safety officer using the vital monitoring application who is given access to monitor one or more users. Additionally, if the monitoring device cannot communicate with the vital monitoring application, data will be stored until such connection can be made. In another example, the present disclosure provides for a system having a plurality of users transmitting through a mobile application their individual vital information to a central application accessibly by a third party user, such as a health professional or a safety officer. The officer can be allowed access to simultaneously view the vital information of the plurality of users. It is further contemplated that the third party is able to send indications and communicate with each of the plurality of users as they see fit. This can significantly improve safety in high risk environments like public safety and fire fighter situations.

FIG. 14 shows an example flow diagram of how the system 400 can be utilized. In this example, the process begins at box 500 where the wearable device is provided to monitor physiological vitals of a user. The process is able to detect heat stress or temperature at box 510, typically through the use of temperature sensors. Measuring heat stress is an indication of dehydration risk. Dehydration risk can lead to box 520 as an indication of various cardiovascular strain. This can be monitored by the ECG and pulse oximetry sensors provided in the vital monitoring device. Accordingly, moving to box 530, cardiac events, or risk of cardiac events, can be predicted.

Referring to FIG. 15, a further example process of the example vital monitoring system is shown. The process begins at box 600 where a wearable device is provided for physiological monitoring. Based on the obtained sensor results, the vital data is analyzed in box 610 which can happen on the mobile application or the remote server as previously described. The vital information can then be displayed to a user through a graphical user interface on the mobile application and/or some sort of heads up display like a helmet as shown schematically at box 640. The analyzed data can further be transmitted and displayed to a third party like a field safety officer or other medical professional as shown at box 620. The analyzed data can then be pushed to a remote server like a cloud server for further review or analysis as shown at box 530.

The following Tables 1-5 provide example data for dimensions and properties for an exemplary device and its component:

TABLE 1

| Device | |
|---|---|
| Physical Specs: | |
| Dimensions | Cylindrical: 53 mm diameter, 20 mm height |
| Weight | Approximately 100 grams |
| Memory | Practically Unlimited due to real-time transmission to mobile phone memory |
| Power Supply | |
| Battery | Li-Po Battery: 3.7 V, 300 mAh |
| Battery Life | 100 hours operational, rechargeable |
| Data Upload | BLUETOOTH Low Energy |
| Software Interface | Various mobile and web-based platforms |

TABLE 2

| ECG Sensing | |
|---|---|
| ECG Channel | Single Channel |
| Frequency Response | 0.5 Hz to 40 Hz |
| A/D Sampling Rate | 300 samples/second |
| Resolution | 16 bit |
| Electrodes | Integrated into device |
| Skin Contact | Any part of the finger (left to right) |
| Material | Silver |

TABLE 3

| Pulse Oximetry | |
|---|---|
| SpO2 Type | Reflective |
| Frequency Response | 0.5 Hz to 40 Hz |
| A/D Sampling Rate | 20 samples/second |
| Resolution | 16 bit |
| SpO2 sensor | Integrated into device |
| Skin Contact | Any finger, typically right index finger |
| Material | Acrylic Glass |

TABLE 4

| Temperature Sensor | |
|---|---|
| Temperature Sensor Type | IR Temperature Sensor |
| A/D Sampling Rate | 1 samples/second |
| Resolution | 16 bit |
| Temperature sensor | Integrated into device |
| Skin Contact | Contactless. Pointed towards the finger. |
| Material | Acrylic Glass |

TABLE 5

| Battery | |
|---|---|
| Standard Capacity | 300 mAh |
| Standard Voltage | 3.7 V |
| Charge Voltage | 4.20 +/− 0.03 V |
| Charge Time | About 3 hours |
| Discharge Cutoff Voltage | 3.0 V |
| Physical Specs: | |
| Dimensions | 6.5 mm thickness, 20 mm width, 30 mm length |
| Weight | 6.8 grams |
| Connector and PCM | Protect circuit module board(PCM) inside, with red(+) and black(−) wire lead out. |

The foregoing disclosure has been illustrated and described in accordance with the relevant legal standards, it is not intended that these examples illustrate and describe all possible forms of the present disclosure, thus the description is exemplary rather than limiting in nature. Variations and modifications to the disclosed examples may become apparent to those skilled in the art and fall within the scope of the present disclosure. Additionally, the features and various implementing examples may be combined to form further examples of the present disclosure.

The invention claimed is:

1. A vital monitoring device comprising:
   (a) a housing defining a disc-like structure extending from an upper surface to a lower surface and having a side portion, the housing enclosing a control unit, the control unit including a microprocessor provided on a circuit board having a plurality of channels formed on the circuit board operable for receiving and processing sensor data, each of the plurality of channels coupled to the microprocessor;
   (b) a pulse oximetry sensor, an electrocardiogram (ECG) sensor, and a temperature sensor provided in the housing and exposed on an exterior surface of the housing and each sensor electronically coupled to a separate and distinct channel formed on the circuit board;
   (c) a wireless communication module provided in the housing coupled to the microprocessor, wherein the wireless communication module is configured to transmit vital data obtained by the plurality of sensors to a remote device having a remote application or remote server;
(d) a first finger depression and a second finger depression formed on the upper surface of the housing and shaped to receive a first and a second finger of one hand of a user, respectively; and
(e) a third finger placement location formed on the side portion of the housing configured to receive a third finger of an opposite hand of the user;
wherein the pulse oximetry sensor is exposed and positioned within the first finger depression, and
wherein the temperature sensor and a first electrode coupled to the ECG sensor are exposed and positioned within the second finger depression and a second electrode coupled to the ECG sensor is exposed and positioned at the third finger placement location to close a circuit for the ECG sensor.

2. The vital monitoring device of claim 1, wherein the wireless communication module is configured to communicate with a mobile device selected from the group consisting of a smart phone, a tablet, a smart watch, a laptop, a computer, and combinations thereof.

3. The vital monitoring device of claim 2, wherein the wireless communication module is configured to communicate with the mobile device having a mobile application, wherein the mobile application is configured to process, display, track, and communicate vital data obtained by the control unit.

4. The vital monitoring device of claim 1, wherein the housing disk-like structure defines a geometry forming a cylindrical disk having a thickness of about 20 mm extending from the upper surface to the lower surface and the side portion extends around a perimeter of the upper surface to the lower surface forming an enclosure and having a diameter of about 55 mm.

5. The vital monitoring device of claim 1, wherein the first finger depression includes a lightguide window to allow the pulse oximetry sensor to transmit and receive signals that engage with the first finger of the user and wherein the pulse oximetry sensor is a reflective type sensor.

6. The vital monitoring device of claim 1, wherein the second finger depression includes a lightguide window positioned corresponding to the temperature sensor to allow the temperature sensor to measure skin temperature of the user.

7. The vital monitoring device of claim 1, wherein the temperature sensor is a contactless temperature sensor including an infrared temperature sensor.

8. A method of monitoring vital data of an individual, the method comprising:
(a) placing the vital monitoring device of claim 1 in contact with the first and the second finger of the one hand of the user and the third finger of the opposite hand of the user;
(b) obtaining pulse oximetry, ECG, and temperature vital data of the user using the vital monitoring device;
(c) transmitting the vital data to the remote device having the remote application through the wireless communication module;
(d) graphically displaying the vital information to the user through the remote device having the remote application.

9. The method of claim 8, further comprising a step of transmitting vital monitoring data to a remote server.

10. A system for vital monitoring of a user, the system comprising:

(a) a vital monitoring device comprising:
(i) a housing defining a disc-like structure extending from an upper surface to a lower surface and having a side portion, the housing enclosing a control unit, the control unit including a microprocessor provided on a circuit board having a plurality of channels formed on the circuit board operable for receiving and processing sensor data, each of the plurality of channels coupled to the microprocessor;
(ii) a pulse oximetry sensor, an electrocardiogram (ECG) sensor, and a temperature sensor provided in the housing and exposed on an exterior surface of the housing and each sensor electronically coupled to a separate and distinct channel formed on the circuit board;
(iii) a wireless communication module provided in the housing coupled to the microprocessor, wherein the wireless communication module is configured to transmit vital data obtained by the pulse oximetry sensor, ECG sensor, and temperature sensor;
(iv) a first finger depression and a second finger depression formed on the upper surface of the housing and shaped to receive a first and a second finger of one hand of a user, respectively; and
(v) a third finger placement location formed on the side portion of the housing configured to receive a third finger of an opposite hand of the user; wherein the pulse oximetry sensor is exposed and positioned within the first finger depression, and wherein the temperature sensor and a first electrode coupled to the ECG sensor are exposed and positioned within the second finger depression and a second electrode coupled to the ECG sensor is exposed and positioned at the third finger placement location to close a circuit for the ECG sensor;
(b) a remote device having a remote application configured to wirelessly communicate with the vital monitoring device and receive the vital data transmitted by the wireless communication module; and
(c) a graphical user interface provided on the remote device and configured to display vital data obtained by the vital monitoring device.

11. The system of claim 10, wherein the remote application is configured to process, display, track, and communicate vital data obtained by the control unit.

12. The system of claim 10, wherein the remote application is configured to diagnose a cardiac condition selected from the group consisting of arrhythmia detection, hyperkalemia, hypercalcemia, Wolf-Parkinson-White syndrome, long QT syndrome, short QT syndrome, Torsades de Pointes, and combinations thereof.

13. The system of claim 10, further comprising a machine learning feature incorporated into the remote application that is configured to determine risk conditions of the user associated with tracking and storing vital data from the user.

14. The system of claim 10, wherein the vital monitoring device includes a wearable component configured to contact a skin of a user and be worn during operation.

15. The system of claim 14, wherein the vital monitoring device is configured to monitor vital data of the user and provide an indication to the user, wherein the indication stimulates the user of a preset condition of the user based on the vital data.

16. The system of claim 15, wherein the preset condition includes a high-risk condition associated with the vital data of the user.

17. The system of claim 15, wherein the indication is a stimulus selected from an auditory signal, a visual signal, and a tactile feedback.

18. The system of claim 10, wherein the vital data obtained by the vital monitoring device is provided to a medical professional through a remote device and wherein the medical professional is provided access to one or more users using the vital monitoring device.

* * * * *